(12) United States Patent
Austen, Jr.

(10) Patent No.: US 10,184,110 B2
(45) Date of Patent: Jan. 22, 2019

(54) SYSTEM AND APPARATUS FOR CELL TREATMENT

(75) Inventor: William G. Austen, Jr., Weston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/814,550

(22) PCT Filed: Aug. 5, 2011

(86) PCT No.: PCT/US2011/046752
§ 371 (c)(1),
(2), (4) Date: Mar. 5, 2013

(87) PCT Pub. No.: WO2012/019103
PCT Pub. Date: Feb. 9, 2012

(65) Prior Publication Data
US 2013/0158515 A1    Jun. 20, 2013

Related U.S. Application Data

(60) Provisional application No. 61/371,400, filed on Aug. 6, 2010.

(51) Int. Cl.
*A61M 5/172*   (2006.01)
*C12N 5/077*   (2010.01)
(Continued)

(52) U.S. Cl.
CPC ....... *C12N 5/0653* (2013.01); *A61M 5/14526* (2013.01); *A61M 5/1723* (2013.01); *C12M 45/02* (2013.01)

(58) Field of Classification Search
CPC ...... A61M 5/14; A61M 5/142; A61M 5/1452; A61M 5/1723; A61M 5/31511
(Continued)

(56) References Cited

U.S. PATENT DOCUMENTS 5,052,999 A    10/1991  Klein
5,212,071 A     5/1993  Fearon et al.
(Continued)

FOREIGN PATENT DOCUMENTS

CA    2715288 A1    8/2009
CN    1741828 A     3/2006
(Continued)

OTHER PUBLICATIONS

Nguyen, et al., Enhanced Fat Protection and Survival in Fat Transplantation via Treatment with Poloxamer 188, Journal of Surgical Research, vol. 151, Issue 2, Feb. 2009, pp. 210-211.*
(Continued)

*Primary Examiner* — Laura A Bouchelle
(74) *Attorney, Agent, or Firm* — Wolf, Greenfield & Sacks, P.C.

(57) ABSTRACT

The present invention relates to systems and apparatuses for improving quality and viability of biological material, such as harvested adipose cells, stem cells, or other cells or biological components, by treatment of the biological material with membrane-repairing/stabilizing agents or the like and/or mechanical removal of components, such as impurities and/or excess treatment agents. The present invention further relates to systems and apparatuses for transplanting tissue, such as adipose tissue.

40 Claims, 18 Drawing Sheets

(51) Int. Cl.
*A61M 5/145* (2006.01)
*C12M 1/33* (2006.01)

(58) Field of Classification Search
USPC ........ 604/131, 151, 154, 218, 246, 208, 209
See application file for complete search history.

(56) References Cited

U.S. PATENT DOCUMENTS

| | | | |
|---|---|---|---|
| 5,256,642 | A | 10/1993 | Fearon et al. |
| 5,470,568 | A | 11/1995 | Lee |
| 5,472,939 | A | 12/1995 | Fearon et al. |
| 5,489,694 | A | 2/1996 | Paust et al. |
| 5,569,670 | A | 10/1996 | Weischer et al. |
| 5,605,687 | A | 2/1997 | Lee |
| 5,621,117 | A | 4/1997 | Bethge et al. |
| 5,650,428 | A | 7/1997 | Ohmori et al. |
| 5,681,561 | A | 10/1997 | Hirshowitz et al. |
| 5,693,664 | A | 12/1997 | Wessel et al. |
| 5,709,868 | A | 1/1998 | Perricone |
| 5,716,404 | A | 2/1998 | Vacanti et al. |
| 5,728,735 | A | 3/1998 | Ulrich et al. |
| 5,856,297 | A | 1/1999 | Fearon et al. |
| 5,965,618 | A | 10/1999 | Perricone |
| 5,981,481 | A | 11/1999 | Fearon et al. |
| 6,090,842 | A | 7/2000 | Packer et al. |
| 6,103,255 | A | 8/2000 | Levene et al. |
| 6,277,842 | B1 | 8/2001 | Carthron |
| 6,316,604 | B1 | 11/2001 | Fearon et al. |
| 6,326,188 | B1 | 12/2001 | Wolfinbarger, Jr. et al. |
| 6,331,559 | B1 | 12/2001 | Bingham et al. |
| 6,353,011 | B1 | 3/2002 | Pershadsingh et al. |
| 6,359,014 | B1 | 3/2002 | Emanuele et al. |
| 6,365,623 | B1 | 4/2002 | Perricone |
| 6,605,637 | B1 | 8/2003 | Harnett et al. |
| 6,673,033 | B1* | 1/2004 | Sciulli et al. ............... 604/67 |
| 6,696,575 | B2 | 2/2004 | Schmidt et al. |
| 7,202,056 | B2 | 4/2007 | Lee et al. |
| 7,220,557 | B2 | 5/2007 | Hastings et al. |
| 7,227,007 | B2 | 6/2007 | Matsuda et al. |
| 7,390,484 | B2 | 6/2008 | Fraser et al. |
| 7,482,152 | B2 | 1/2009 | Ramasubramanian |
| 7,588,732 | B2 | 9/2009 | Buss |
| 7,700,086 | B2 | 4/2010 | Schwarz |
| 7,723,085 | B2 | 5/2010 | Smith et al. |
| 7,824,847 | B2 | 11/2010 | Steinhardt |
| 8,067,359 | B2 | 11/2011 | Hayes et al. |
| 8,071,085 | B2 | 12/2011 | Ito et al. |
| 8,512,695 | B2 | 8/2013 | Austen |
| 8,790,519 | B2* | 7/2014 | Leach ............ B01D 21/0012 210/321.67 |
| 2002/0016570 | A1 | 2/2002 | Cartledge |
| 2002/0042372 | A1 | 4/2002 | Olsen et al. |
| 2002/0012642 | A1 | 12/2002 | Perricone |
| 2003/0054374 | A1 | 3/2003 | Ramanathan et al. |
| 2003/0092017 | A1 | 5/2003 | Finger |
| 2003/0092900 | A1 | 5/2003 | Iruela-Arispe et al. |
| 2003/0118545 | A1 | 6/2003 | Shi et al. |
| 2003/0162189 | A1 | 8/2003 | Lee et al. |
| 2003/0180337 | A1 | 9/2003 | Streicher et al. |
| 2003/0224450 | A1 | 12/2003 | Lee et al. |
| 2003/0224486 | A1 | 12/2003 | Carman et al. |
| 2004/0002449 | A1 | 1/2004 | Iruela-Arispe et al. |
| 2004/0002509 | A1 | 1/2004 | Adams |
| 2004/0018976 | A1 | 1/2004 | Feder et al. |
| 2004/0025195 | A1 | 2/2004 | Lee et al. |
| 2004/0030098 | A1 | 2/2004 | Lee et al. |
| 2004/0081986 | A1 | 4/2004 | Matsuda et al. |
| 2004/0086896 | A1 | 5/2004 | Carman et al. |
| 2004/0087543 | A1 | 5/2004 | Shriver et al. |
| 2004/0116350 | A1 | 6/2004 | Wentworth, Jr. et al. |
| 2004/0191225 | A1* | 9/2004 | Dinsmore ............ A61K 9/0019 424/93.7 |
| 2004/0198658 | A1 | 10/2004 | Olsen et al. |
| 2004/0204576 | A1 | 10/2004 | Jackson et al. |
| 2004/0265345 | A1 | 12/2004 | Perricone |
| 2004/0265388 | A1 | 12/2004 | Zhang et al. |
| 2005/0025755 | A1* | 2/2005 | Hedrick ............ A61L 27/3604 424/93.21 |
| 2005/0069520 | A1 | 3/2005 | Shi et al. |
| 2005/0079161 | A1* | 4/2005 | Alt ................. 424/93.7 |
| 2005/0084961 | A1* | 4/2005 | Hedrick et al. ............... 435/366 |
| 2005/0118632 | A1 | 6/2005 | Chen et al. |
| 2005/0158358 | A1 | 7/2005 | West et al. |
| 2005/0175665 | A1 | 8/2005 | Hunter et al. |
| 2005/0232902 | A1 | 10/2005 | Kofidis |
| 2006/0121016 | A1 | 6/2006 | Lee |
| 2006/0127384 | A1 | 6/2006 | Capaccioli et al. |
| 2006/0182725 | A1 | 8/2006 | Marko et al. |
| 2006/0184101 | A1 | 8/2006 | Srinivasan et al. |
| 2006/0213374 | A1* | 9/2006 | Shippert ............ A61M 1/0062 99/472 |
| 2007/0071743 | A1 | 3/2007 | Lee et al. |
| 2007/0087320 | A1 | 4/2007 | Licari et al. |
| 2007/0110731 | A1 | 5/2007 | Riley |
| 2007/0237740 | A1 | 10/2007 | Reddington et al. |
| 2008/0118447 | A1 | 5/2008 | Nathoo et al. |
| 2009/0017438 | A1 | 1/2009 | Roy et al. |
| 2009/0017439 | A1 | 1/2009 | Shimko et al. |
| 2009/0239299 | A1 | 9/2009 | Buss |
| 2010/0104542 | A1 | 4/2010 | Austen |
| 2010/0268189 | A1* | 10/2010 | Byrnes et al. ............... 604/506 |
| 2011/0183001 | A1 | 7/2011 | Rosson et al. |
| 2011/0313345 | A1 | 12/2011 | Schafer |
| 2012/0128641 | A1 | 5/2012 | Austen, Jr. |
| 2013/0336936 | A1 | 12/2013 | Austen |

FOREIGN PATENT DOCUMENTS

| | | |
|---|---|---|
| CN | 101400392 A | 4/2009 |
| CN | 101489605 A | 7/2009 |
| EP | 0 427 247 A2 | 5/1991 |
| JP | H10-510736 A | 10/1998 |
| JP | 2007-524396 A | 8/2007 |
| JP | 2010-063441 A | 3/2010 |
| WO | WO 89/09220 A1 | 10/1989 |
| WO | WO 91/05047 A1 | 4/1991 |
| WO | WO 93/15745 A1 | 8/1993 |
| WO | WO 96/18424 A1 | 6/1996 |
| WO | WO 99/61440 A1 | 12/1999 |
| WO | WO 00/50639 A2 | 8/2000 |
| WO | WO 00/77164 A1 | 12/2000 |
| WO | WO 01/30969 A2 | 5/2001 |
| WO | WO 02/16557 A2 | 2/2002 |
| WO | WO 02/072755 A2 | 9/2002 |
| WO | WO 02/077173 A2 | 10/2002 |
| WO | WO 02/086076 A2 | 10/2002 |
| WO | WO 02/092107 A1 | 11/2002 |
| WO | WO 03/012063 A2 | 2/2003 |
| WO | WO 03/083078 A2 | 10/2003 |
| WO | WO 2004/039940 A2 | 5/2004 |
| WO | WO 2004/048529 A2 | 6/2004 |
| WO | WO 2004/067065 A1 | 8/2004 |
| WO | WO 2004/094621 A2 | 11/2004 |
| WO | WO 2004/100886 A2 | 11/2004 |
| WO | WO 2005/012480 A2 | 2/2005 |
| WO | WO 2005/072343 A2 | 8/2005 |
| WO | WO 2006/037031 A2 | 4/2006 |
| WO | WO 2006/044738 A2 | 4/2006 |
| WO | WO 2007/005668 A2 | 1/2007 |
| WO | WO 2007/009285 A1 | 1/2007 |
| WO | WO 2007/080919 A1 | 7/2007 |
| WO | WO 2009/102452 A2 | 8/2009 |
| WO | WO 2010/047793 A2 | 4/2010 |
| WO | WO 2010/130304 A1 | 11/2010 |
| WO | WO 2011/059733 A2 | 5/2011 |
| WO | WO 2012/019103 A2 | 2/2012 |

OTHER PUBLICATIONS

International Search Report and Written Opinion for PCT/US2009/005727, dated Jun. 4, 2010.
International Preliminary Report on Patentability for PCT/US2009/005727, dated May 5, 2011.

(56) References Cited

OTHER PUBLICATIONS

Extended European Search Report for EP 10802547.9, dated Jan. 14, 2013.
International Search Report and Written Opinion for PCT/US2010/002033, dated Apr. 28, 2011.
International Preliminary Report on Patentability for PCT/US2010/002033, dated Feb. 2, 2012.
International Search Report and Written Opinion for PCT/US2010/054451, dated Jul. 20, 2011.
International Preliminary Report on Patentability for PCT/US2010/054451, dated May 10, 2012.
Invitation to Pay Additional Fees for PCT/US2011/046752, dated Nov. 29, 2011.
International Search Report and Written Opinion for PCT/US2011/046752, dated Feb. 23, 2012.
International Preliminary Report on Patentability for PCT/US2011/046752, dated Feb. 21, 2013.
Office Communication, dated Aug. 14, 2012, for U.S. Appl. No. 12/603,075.
Office Communication, dated Feb. 22, 2013, for U.S. Appl. No. 12/603,075.
Interview Summary, dated May 24, 2013, for U.S. Appl. No. 12/603,075.
Notice of Allowance, dated Jun. 7, 2013, for U.S. Appl. No. 12/603,075.
Agarwal et al., Multimodal strategies for resuscitating injured cells. Ann N Y Acad Sci. Dec. 2005;1066:295-309.
Al-Rubeai et al., Cell cycle and cell size dependence of susceptibility to hydrodynamic forces. Biotechnol Bioeng. Apr. 5, 1995;46(1):88-92.
Anthony et al., Pluronic F-68 increases the post-thaw growth of cryopreserved plant cells. Cryobiology. 1996;33:508-14.
Baczkó et al., Pharmacological activation of plasma-membrane KATP channels reduces reoxygenation-induced Ca(2+) overload in cardiac myocytes via modulation of the diastolic membrane potential. Br J Pharmacol. Mar. 2004;141(6):1059-67. Epub Mar. 1, 2004.
Birchenough et al., Topical poloxamer-188 improves blood flow following thermal injury in rat mesenteric microvasculature. Ann Plast Surg. May 2008;60(5):584-8.
Boodhwani et al., Effects of purified poloxamer 407 gel on vascular occlusion and the coronary endothelium. Eur J Cardiothorac Surg. May 2006;29(5):736-41. Epub Apr. 12, 2006.
Borgens et al., Subcutaneous tri-block copolymer produces recovery from spinal cord injury. J Neurosci Res. Apr. 1, 2004;76(1):141-54.
Boschert et al., Analysis of lipocyte viability after liposuction. Plast Reconstr Surg. Feb. 2002;109(2):761-5.
Bustamante et al., Alpha-lipoic acid in liver metabolism and disease. Free Radic Biol Med. Apr. 1998;24(6):1023-39.
Cadichon et al., Neuroprotective effect of the surfactant poloxamer 188 in a model of intracranial hemorrhage in rats. J Neurosurg. Jan. 2007;106(1 Suppl):36-40.
Cho et al., Alpha-lipoic acid decreases thiol reactivity of the insulin receptor and protein tyrosine phosphatase 1B in 3T3-L1 adipocytes. Biochem Pharmacol. Sep. 1, 2003;66(5):849-58.
Coleman, Structural fat grafts: the ideal filler? Clin Plast Surg. Jan. 2001;28(1):111-9.
Curry et al., Poloxamer 188 volumetrically decreases neuronal loss in the rat in a time-dependent manner. Neurosurgery. Oct. 2004;55(4):943-8; discussion 948-9.
Diesel et al., Alpha-lipoic acid as a directly binding activator of the insulin receptor: protection from hepatocyte apoptosis. Biochemistry. Feb. 27, 2007;46(8):2146-55. Epub Feb. 3, 2007.
Duenschede et al., Protective effects of ischemic preconditioning and application of lipoic acid prior to 90 min of hepatic ischemia in a rat model. World J Gastroenterol. Jul. 21, 2007;13(27):3692-8.
Dulundu et al., Alpha-lipoic acid protects against hepatic ischemia-reperfusion injury in rats. Pharmacology. 2007;79(3):163-70. Epub Jan. 24, 2007.
Eto et al., Characterization of structure and cellular components of aspirated and excised adipose tissue. Plast Reconstr Surg. Oct. 2009;124(4):1087-97.
Ferguson et al., The viability of autologous fat grafts harvested with the LipiVage system: a comparative study. Ann Plast Surg. May 2008;60(5):594-7.
Forman et al., Role of perfluorochemical emulsions in the treatment of myocardial reperfusion injury. Am Heart J. Nov. 1992;124(5):1347-57.
Gimble et al., Adipose-derived stem cells for regenerative medicine. Circ Res. May 11, 2007;100(9):1249-60.
Giugliano et al., Liposuction and lipoinjection treatment for congenital and acquired lipodystrophies in children. Plast Reconstr Surg. Jul. 2009;124(1):134-43.
Gonzalez et al., An alternative method for harvest and processing fat grafts: an in vitro study of cell viability and survival. Plast Reconstr Surg. Jul. 2007;120(1):285-94.
González Hernández et al., Serum-free culturing of mammalian cells—adaptation to and cryopreservation in fully defined media. ALTEX. 2007;24(2):110-6.
Greene et al., alpha-Lipoic acid prevents the development of glucose-induced insulin resistance in 3T3-L1 adipocytes and accelerates the decline in immunoreactive insulin during cell incubation. Metabolism. Sep. 2001;50(9):1063-9.
Greenebaum et al., Poloxamer 188 prevents acute necrosis of adult skeletal muscle cells following high-dose irradiation. Burns. Sep. 2004;30(6):539-47.
Gull et al., Viability of the human adenocarcinoma cell line Caco-2: Influence of cryoprotectant, freezing rate, and storage temperature. Sci Pharm. 2009;77:133-41.
Gutowski, Current applications and safety of autologous fat grafts: a report of the ASPS fat graft task force. Plast Reconstr Surg. Jul. 2009;124(1):272-80.
Hannig et al., Surfactant sealing of membranes permeabilized by ionizing radiation. Radiat Res. Aug. 2000;154(2):171-7.
Haramaki et al., Cytosolic and mitochondrial systems for NADH- and NADPH-dependent reduction of alpha-lipoic acid. Free Radic Biol Med. 1997;22(3):535-42.
Hyakusoku et al., Complications after autologous fat injection to the breast. Plast Reconstr Surg. Jan. 2009;123(1):360-70.
Justicz et al., Reduction of myocardial infarct size by poloxamer 188 and mannitol in a canine model. Am Heart J. Sep. 1991;122(3 Pt 1):671-80.
Kaufman et al., Autologous fat transfer national consensus survey: trends in techniques for harvest, preparation, and application, and perception of short- and long-term results. Plast Reconstr Surg. Jan. 2007;119(1):323-31.
Kelly et al., Effect of Poloxamer 188 on Collateral Blood Flow, Myocardial Infarct Size, and Left Ventricular Function in a Canine Model of Prolonged (3-Hour) Coronary Occlusion and Reperfusion. J Thromb Thrombolysis. Jul. 1998;5(3):239-47.
Khattak et al., Pluronic F127 as a cell encapsulation material: utilization of membrane-stabilizing agents. Tissue Eng. May-Jun. 2005;11(5-6):974-83.
Kiemer et al., Inhibition of LPS-induced nitric oxide and TNF-alpha production by alpha lipoic acid in rat Kupffer cells and in RAW 264.7 murine macrophages. Immunol Cell Biol. Dec. 2002;80(6):550-7.
Kolodgie et al., Hyperoxic reperfusion is required to reduce infarct size after intravenous therapy with perfluorochemical (Fluosol-DA 20%) or its detergent component (poloxamer 188) in a poorly collateralized animal model. Absence of a role of polymorphonuclear leukocytes. J Am Coll Cardiol. Oct. 1994;24(4):1098-108.
Kurita et al., Influences of centrifugation on cells and tissues in liposuction aspirates: optimized centrifugation for lipotransfer and cell isolation. Plast Reconstr Surg. Mar. 2008;121(3):1033-41.
Lam et al., Limitations, complications, and long-term sequelae of fat transfer. Facial Plast Surg Clin North Am. Nov. 2008;16(4):391-9.
Lee et al., Direct observation of the p188 mediated membrane sealing with atomic force microscopy. MCB. 2006;3(4):185-6.
Lee et al., A novel approach to adipocyte analysis. Plast Reconstr Surg. Feb. 2012;129(2):380-7.

(56) References Cited

OTHER PUBLICATIONS

Lee et al., Surfactant-induced sealing of electropermeabilized skeletal muscle membranes in vivo. Proc Natl Acad Sci U S A. May 15, 1992;89(10):4524-8.

Liu et al., Neuroprotective Effect of lipoic acid in Cerebral Ischemia-reperfusion Injury of Rats. Chin J Vet Sci. Jul. 2004;24(4):388-90. Chinese.

Lowe et al., Beneficial effects of Pluronic F-68 and artificial oxygen carriers on the post-thaw recovery of cryopreserved plant cells. Artif Cells Blood Substit Immobil Biotechnol. Jul. 2001;29(4):297-316.

Marks et al., Amphiphilic, tri-block copolymers provide potent membrane-targeted neuroprotection. FASEB J. Apr. 2001;15(6):1107-9.

Maskarinec et al., Direct observation of poloxamer 188 insertion into lipid monolayers. Biophys J. Mar. 2002;82(3):1453-9.

Maskarinec et al., Membrane sealing by polymers. Ann N Y Acad Sci. Dec. 2005;1066:310-20.

Maynard et al., Randomized, controlled trial of RheothRx (poloxamer 188) in patients with suspected acute myocardial infarction. RheothRx in Myocardial Infarction Study Group. Am Heart J. May 1998;135(5 Pt 1):797-804.

Medina et al., A high-throughput model for fat graft assessment. Lasers Surg Med. Dec. 2009;41(10):738-44.

Medina et al., Polymer therapy: A novel treatment to improve fat graft viability. Plast Reconstr Surg. Jun. 2011;127(6):2270-82.

Merchant et al, Poloxamer 188 enhances functional recovery of lethally heat-shocked fibroblasts. J Surg Res. Feb. 1, 1998;74(2):131-40.

Mina et al., Poloxamer 188 copolymer membrane sealant rescues toxicity of amyloid oligomers in vitro. J Mol Biol. Aug. 21, 2009;391(3):577-85. Epub Jun. 12, 2009.

Moini et al., R-alpha-lipoic acid action on cell redox status, the insulin receptor, and glucose uptake in 3T3-L1 adipocytes. Arch Biochem Biophys. Jan. 15, 2002;397(2):384-91.

Monteiro et al., Adipocyte size and liability to cell death. Obes Surg. Jun. 2006;16(6):804-6.

Müller et al., Alpha-lipoic acid preconditioning reduces ischemia-reperfusion injury of the rat liver via the PI3-kinase/Akt pathway. Am J Physiol Gastrointest Liver Physiol. Oct. 2003;285(4):G769-78. Epub Jun. 19, 2003.

Nguyen et al., Enhanced Fat Protection and Survival in Fat Transplantation via Treatment with Poloxamer 188. IFATS08 Symposium 6. France. Oct. 2008. Journal of Surgical Research. Feb. 2, 2009; 151(2); 210-11. Abstract 87.

Nishimura et al., Microvascular angiogenesis and apoptosis in the survival of free fat grafts. Laryngoscope. Aug. 2000;110(8):1333-8.

O'Keefe et al., Poloxamer-188 as an adjunct to primary percutaneous transluminal coronary angioplasty for acute myocardial infarction. Am J Cardiol. Oct. 1, 1996;78(7):747-50.

Ogawa et al., The effect of hydrostatic pressure on three-dimensional chondroinduction of human adipose-derived stem cells. Tissue Eng Part A. Oct. 2009;15(10):2937-45.

Packer, alpha-Lipoic acid: a metabolic antioxidant which regulates NF-kappa B signal transduction and protects against oxidative injury. Drug Metab Rev. May 1998;30(2):245-75.

Palmer et al., Surfactant administration reduces testicular ischemia-reperfusion injury. J Urol. Jun. 1998;159(6):2136-9.

Pearson, Human genetics: One gene, twenty years. Nature. Jul. 2009;460:164-9. Erratum in Nature. Jul. 16, 2009;460(7253):317.

Pessler et al., Oxidative stress impairs nuclear proteins binding to the insulin responsive element in the GLUT4 promoter. Diabetologia. Dec. 2001;44(12):2156-64.

Potier et al., Prolonged hypoxia concomitant with serum deprivation induces massive human mesenchymal stem cell death. Tissue Eng. Jun. 2007;13(6):1325-31.

Pu et al., Autologous fat grafts harvested and refined by the Coleman technique: a comparative study. Plast Reconstr Surg. Sep. 2008;122(3):932-7.

Pu et al., The viability of fatty tissues within adipose aspirates after conventional liposuction: a comprehensive study. Ann Plast Surg. Mar. 2005;54(3):288-92; discussion 292.

Quinn et al., Adjunctive use of the non-ionic surfactant Poloxamer 188 improves fetal dopaminergic cell survival and reinnervation in a neural transplantation strategy for Parkinson's disease. Eur J Neurosci. Jan. 2008;27(1):43-52. Epub Dec. 15, 2007.

Ramon et al., Enhancing the take of injected adipose tissue by a simple method for concentrating fat cells. Plast Reconstr Surg. Jan. 2005;115(1):197-201.

Rohrich et al., In search of improved fat transfer viability: a quantitative analysis of the role of centrifugation and harvest site. Plast Reconstr Surg. Jan. 2004;113(1):391-5.

Roy et al., Antioxidant regulation of phorbol ester-induced adhesion of human Jurkat T-cells to endothelial cells. Free Radic Biol Med. Jul. 15, 1998;25(2):229-41.

Roy et al., Redox regulation of cell functions by alpha-lipoate: biochemical and molecular aspects. Biofactors. 1998;7(3):263-7.

Rudich et al., Lipoic acid protects against oxidative stress induced impairment in insulin stimulation of protein kinase B and glucose transport in 3T3-L1 adipocytes. Diabetologia. Aug. 1999;42(8):949-57.

Schaer et al., Beneficial effects of RheothRx injection in patients receiving thrombolytic therapy for acute myocardial infarction. Results of a randomized, double-blind, placebo-controlled trial. Circulation. Aug. 1, 1996;94(3):298-307.

Schaer et al., Reduction in reperfusion-induced myocardial necrosis in dogs by RheothRx injection (poloxamer 188 N.F.), a hemorheological agent that alters neutrophil function. Circulation. Dec. 1994;90(6):2964-75.

Schmolka, A review of block polymer surfactants. J Am Oil Chem Soc. 1977;54(3):110-6.

Serbest et al., Mechanisms of cell death and neuroprotection by poloxamer 188 after mechanical trauma. FASEB J. Feb. 2006;20(2):308-10. Epub Dec. 21, 2005.

Serbest et al., The effect of poloxamer-188 on neuronal cell recovery from mechanical injury. J Neurotrauma. Jan. 2005;22(1):119-32.

Shen et al., R-alpha-lipoic acid and acetyl-L-carnitine complementarily promote mitochondrial biogenesis in murine 3T3-L1 adipocytes. Diabetologia. Jan. 2008;51(1):165-74. Epub Nov. 17, 2007.

Singh-Joy et al., Safety assessment of poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate as used in cosmetics. Int J Toxicol. 2008;27 Suppl 2:93-128.

Suga et al., Numerical measurement of viable and nonviable adipocytes and other cellular components in aspirated fat tissue. Plast Reconstr Surg. Jul. 2008;122(1):103-13.

Thanik et al., A murine model for studying diffusely injected human fat. Plast Reconstr Surg. Jul. 2009;124(1):74-81.

Tharmalingam et al., Pluronic enhances the robustness and reduces the cell attachment of mammalian cells. Mol Biotechnol. Jun. 2008;39(2):167-77.

Vashi et al., Adipose differentiation of bone marrow-derived mesenchymal stem cells using Pluronic F-127 hydrogel in vitro. Biomaterials. Feb. 2008;29(5):573-9. Epub Nov. 5, 2007.

Watanabe et al., Lysophosphatidylcholine-induced myocardial damage is inhibited by pretreatment with poloxamer 188 in isolated rat heart. Mol Cell Biochem. Jun. 2003;248(1-2):209-15.

Wlotzka et al., In vivo properties of an anti-GnRH Spiegelmer: an example of an oligonucleotide-based therapeutic substance class. Proc Natl Acad Sci U S A. Jun. 25, 2002;99(13):8898-902. Epub Jun. 17, 2002.

Wu et al., Effects of poloxamer 188 on phospholipid monolayer morphology: an atomic force microscopy study. Langmuir. Feb. 17, 2009;25(4):2133-9.

Wu et al., Interaction between lipid monolayers and poloxamer 188: an X-ray reflectivity and diffraction study. Biophys J. Nov. 2005;89(5):3159-73. Epub Aug. 12, 2005.

Yamaguchi et al., Revascularization determines volume retention and gene expression by fat grafts in mice. Exp Biol Med (Maywood). Nov. 2005;230(10):742-8.

(56) References Cited

OTHER PUBLICATIONS

Yasuda et al., Dystrophic heart failure blocked by membrane sealant poloxamer. Nature. Aug. 18, 2005;436(7053):1025-9. Epub Jul. 17, 2005.
Yi et al., Enhancement of viability of fat grafts in nude mice by endothelial progenitor cells. Dermatol Surg. Dec. 2006;32(12):1437-43.
Zhang et al., Effect of Pluronic F-68 on the mechanical properties of mammalian cells. Enzyme Microb Technol. Dec. 1992;14(12):980-3.
Zhu et al., Hypoxia and serum deprivation-induced apoptosis in mesenchymal stem cells. Stem Cells. Feb. 2006;24(2):416-25. Epub Oct. 27, 2005.
Zhu et al., Supplementation of fat grafts with adipose-derived regenerative cells improves long-term graft retention. Ann Plast Surg. Feb. 2010;64(2):222-8.
Extended European Search Report for EP 09822316.7, dated Dec. 5, 2013.
Extended European Search Report for EP 11815375.8, dated Feb. 13, 2014.
[No Author Listed] STN Registry Submission; Registry file for RN 691397-13-4 entered Jun. 10, 2004. Downloaded Jan. 21, 2014. 11 pages.
Buhr et al., Frozen-thawed boar sperm: Isolation of membranes and fluidity measurement. Reproduction in Domestic Animals. 1996;31(1):147-152.
Cai et al., Effect of F68 and its combination with dimethyl sulfoxide on cryopreserved hematopoietic stem cell from umbilical cord blood. Di-San Junyi Daxue Xuebao (Acta Acdaemiae Medicinae Militaris Tertiae). 2002;24(11):1293-95. Chinese.
Kabanov et al., Pluronic block copolymers: novel functional molecules for gene therapy. Adv Drug Deliv Rev. Feb. 21, 2002;54(2):223-33.
Morille et al., New PLGA-P188-PLGA matrix enhances TGF-β3 release from pharmacologically active microcarriers and promotes chondrogenesis of mesenchymal stem cells. J Control Release. Aug. 28, 2013;170(1):99-110. doi: 10.1016/j.jconrel.2013.04.017. Epub May 3, 2013.
Moscatello et al., Cryopreservation of human fat for soft tissue augmentation: viability requires use of cryoprotectant and controlled freezing and storage. Dermatol Surg. Nov. 2005;31(11 Pt 2):1506-10.
Alvarez-Lorenzo et al., Poloxamine-based nanomaterials for drug delivery. Front Biosci (Elite Ed). Jan. 1, 2010;2:424-40.
Hernandez et al., Serum-free culturing of mammalian cells—adaptation to and cryopreservation in fully defined media. ALTEX. 2007;24(2):110-6.
Lalikos et al., Biochemical assessment of cellular damage after adipocyte harvest. J Surg Res. Jun. 1997;70(1):95-100.
Maskarinec et al., Comparative study of Poloxamer Insertion into Lipid Monolayers. Langmuir 2003 19: 1809-1815.
Pickett-Gies et al., Characterization of the isolated rat flexor digitorum brevis for the study of skeletal muscle phosphorylase kinase phosphorylation. J Biol Chem. Mar. 5, 1987;262(7):3227-38.
Thirumala et al., Effect of various freezing parameters on the immediate post-thaw membrane integrity of adipose tissue derived adult stem cells. Biotechnol Prog. Sep.-Oct. 2005;21(5):1511-24.
Wolter et al., Cryopreservation of mature human adipocytes: in vitro measurement of viability. Ann Plast Surg. Oct. 2005;55(4):408-13.
Bunnell et al., Adipose-derived stem cells: isolation, expansion and differentiation. Methods. Jun. 2008;45(2):115-20. doi: 10.1016/j.ymeth.2008.03.006. Epub May 29, 2008.
Kim et al., Functional Viability of Chondrocytes Stored at 4 degrees C. Tissue Eng. 1996 Spring;2(1):75-81. doi: 10.1089/ten.1996.2.75.
Smith et al., Survival of frozen chondrocytes isolated from cartilage of adult mammals. Nature. Feb. 20, 1965;205(4973):782-784.
Cao et al., Comparative study of the use of poly(glycolic acid), calcium alginate and pluronics in the engineering of autologous porcine cartilage. J Biomater Sci Polym Ed. 1998;9(5):475-87.
Gau-Racine et al., PEO-PPO block copolymer vectors do not interact directly with DNA but with lipid membranes. J Phys Chem B. Aug. 23, 2007;111(33):9900-7. Epub Jul. 28, 2007.
Park et al., Thermosensitive and Cell-Adhesive Pluronic Hydrogels for Human Adipose-Derived Stem Cells. Key Engineering Materials. Jul. 2007;342-343:301-304.
U.S. Appl. No. 12/603,075, filed Oct. 21, 2009, Austen, Jr.
U.S. Appl. No. 13/970,978, filed Aug. 20, 2013, Austen, Jr.
U.S. Appl. No. 13/386,073, filed Feb. 13, 2012, Austen, Jr.
EP 09822316.7, Dec. 5, 2013, Extended European Search Report.
EP 11815375.8, Feb. 13, 2014, Extended European Search Report.

\* cited by examiner

| 3cc syringe | | 10cc syringe | | 60cc syringe | |
|---|---|---|---|---|---|
| Suction | Pressure | Suction | Pressure | Suction | Pressure |
| 1 | -415 | 1 | -380 | 10 | -682 |
| 2 | -542 | 2 | -513 | 20 | -713 |
| 3 | -613 | 3 | -580 | 30 | -724 |
|   |      | 4 | -630 | 40 | -729 |
|   |      | 5 | -653 | 50 | -732 |
|   |      | 6 | -661 | 60 | -733 |
|   |      | 7 | -679 |    |      |
|   |      | 8 | -683 |    |      |
|   |      | 9 | -691 |    |      |
|   |      | 10 | -696 |   |      |

SYSTEM AND APPARATUS FOR CELL TREATMENT

RELATED APPLICATIONS

This application is a national stage filing under 35 U.S.C. § 371 of international PCT application PCT/US2011/046752, filed Aug. 5, 2011, which claims the benefit under 35 U.S.C. § 119(e) of U.S. provisional application, U.S. Ser. No. 61/371,400, filed Aug. 6, 2010, and entitled "SYSTEM AND APPARATUS FOR CELL TREATMENT," the entire contents of each of which are incorporated herein by reference.

FIELD OF THE INVENTION

The present invention relates to methods, systems and apparatuses for processing biological material, such as harvested adipose tissue, adipose cells (adipocytes), stem cells, or other cells or tissues.

BACKGROUND INFORMATION

Adipose tissue that is harvested from the body can be re-introduced or autologously transplanted, e.g., as a filler material for cosmetic purposes such as augmentation of certain body features. Adipose tissue may also be used for certain reconstructive and/or functional procedures such as facial reconstruction, breast reconstruction or augmentation, and vocal cord injection to improve voice function. The adipose tissue can be harvested using conventional liposuction procedures or other techniques. Such harvested adipose tissue often includes other agents, such as water or other liquids, free lipids, blood cells, etc., in addition to the adipose cells (adipocytes).

Removal of impurities and/or fluid from the harvested adipose tissue prior to reintroducing the adipocytes into a patient's body may be beneficial to graft success. Several procedures and systems have been developed to achieve this separation or "purification" of the fat. Many procedures (including that used in the Coleman System) involve the use of a centrifuge to segregate the different components of the harvested adipose tissue and allow them to be separated. Another system, the PUREGRAFT system, uses a squeegee-type squeezing motion on adipose tissue placed in a plastic IV bag to achieve some separation of adipose cells from the other components of the adipose tissue. The "purified" adipose cells can then be reintroduced into the body using a syringe, cannula, or the like.

A mechanical segregation process, such as a centrifuge or squeegee process, may inflict damage on adipose cells and reduce their viability, leading to increased apoptosis and cell death. Such damage can arise from excessive forces (e.g., shear forces) or pressures that can arise during the purification/segregation procedures. Damaged adipocytes that die after transplantation tend to be resorbed by the body, reducing the effectiveness of the transplantation procedure.

The overall viability of adipocytes can be improved by exposing them to certain classes of polymers such as Poloxamer P188, a triblock copolymer, and/or antioxidants such as lipoic acid. Thus, a fat harvesting/purification system that provides for treatment of the harvested adipose tissue using such agents, which can act as membrane stabilization agents (MSAs) or cell protectants, to improve viability of the adipose cells may be desirable for, e.g., fat harvesting and autologous fat transplantation procedures.

Thus, there is a need for a relatively simple, inexpensive, effective and safe device configured to provide some segregation of adipose cells from other undesired components of the tissue while limiting the mechanical damage to the cells. It is also desirable to provide such a system that does not require a centrifuge or other large or expensive piece of equipment and that can be used in an operating room or physician's office. It is further desirable to provide a treatment system for harvested adipose tissue that facilitates treatment of the adipose cells with appropriate agents to improve the viability of the cells to be transplanted.

SUMMARY OF THE INVENTION

Embodiments of the present invention provide methods, systems, and apparatuses for processing biological cells or tissues that have been removed from a subject, and which may optionally be transplanted into the same or a different subject. Such processing can include removal of impurities, e.g., excess liquids, free lipids, blood cells, or other components of the biological material that may be undesirable, and/or adding certain agents to the biological material to achieve certain effects, (e.g. improving viability of the graft), and optionally removing an excess of such agents before transplantation of the biological material into a subject.

For example, improving the viability of adipose cells and/or other cells found in adipose tissue (e.g., stem cells) for transplantation can be achieved by mixing harvested adipose tissue with a membrane stabilization agent (MSA) or cell protectant such as Poloxamer P188 or lipoic acid. (See, e.g., International PCT Application No. PCT/US2009/005727 and U.S. Patent Application Publication No. 2010/0104542, the contents of which are incorporated herein by reference in their entireties). The apparatus can optionally provide separation of adipose cells from undesired components of the harvested biological material (e.g., excess fluid, blood, free lipids) using a mechanical force, such as a plunger mechanism with a filter element, or using positive or negative pressure. A force-limiting arrangement can be provided with the plunger to limit the amount of force/pressure applied to the adipose cells, thereby limiting the amount of mechanical damage that may be induced. Impurities and/or fluids, such as tumescent fluid or free lipid, can also be removed from the adipose tissue by providing a retention matrix (e.g., a matrix composed of an absorbent material and/or adsorbent material) in contact with the adipose tissue.

According to some aspects of the invention, apparatuses and systems are provided for processing and optionally transplanting biological materials, e.g., injecting biological materials into a graft site in a subject. The apparatuses typically include a chamber having at least one outlet, and a pressure generating device configured and arranged for generating a positive pressure within the chamber that is at or below a predetermined threshold. The positive pressure is generally sufficient to cause the biological material, if present in the chamber, to discharge through the outlet, and the predetermined threshold is generally at a pressure above which the biological material has relatively low viability as a tissue graft following discharge from the outlet into a graft site in the subject.

According to some aspects of the invention, apparatuses and systems disclosed herein provide improved methods for injecting biological materials into graft sites in a subject. Accordingly, methods are provided herein for injecting processed biological materials into one or more graft sites in a subject. In some embodiments, the methods involve loading a biological material into the chamber of an apparatus and causing the pressure generating device of the apparatus to generate a positive pressure within the chamber that is at or below the predetermined threshold to cause the biological material to discharge through the outlet. In general, the predetermined threshold is a pressure above which the biological material has relatively low viability as a tissue graft following discharge from the outlet into a graft site in a subject. Decreased viability may result from tissue or cell damage caused by relatively high flow rates, pressures, injection velocities and/or shear stresses imposed upon the biological material, particularly cells, during processing or injection.

In other aspects of the invention, systems are provided for processing biological materials. The systems are typically utilized for processing adipose tissue obtained from a subject at one location, typically as a lipoaspirate, for autologous fat transfer into the subject at a different location. The fat processing and transfer are typically performed for cosmetic or reconstructive purposes. The systems typically include a chamber having at least one inlet and at least one outlet, a pressure generating device configured and arranged for transferring a biological material into the chamber through the at least one inlet and discharging a processed biological material out from the chamber through the at least one outlet. At least one retention matrix is typically present within the chamber. This retention matrix is typically configured and arranged for contacting the biological material, when present in the chamber, such that a component (e.g., fluid) of the biological material is retained in the retention matrix. The systems may include a variety of other components in addition to the retention matrix for purposes of removing undesirable components from the harvested biological material. For example, the systems may include filters, antigen-binding regions for sequestering target antigens (e.g., cells, soluble proteins, growth factors), and antioxidants for sequestering free radicals, and may also include components for delivering additives to the biological materials, e.g., membrane stabilization agents. In certain embodiments, the system is a modular system that includes multiple components (e.g., filters, endpieces, cannulas, caps, retention matrices, chambers) that may be used as needed.

Definitions

"Approximately" or "about" when used in reference to a number generally includes numbers that fall within a range of 5% in either direction of the number (greater than or less than the number) unless otherwise stated or otherwise evident from the context (e.g., where such number would exceed 100% of a possible value).

"Adipocyte" or "adipose cell" refers to a cell that is capable of synthesizing and/or storing fatty acids. The term includes adipocytes with the properties representative of those of cells present within white fat, yellow fat, and/or brown fat. Typically, adipocytes store energy in the form of lipids and release energy stores in response to hormonal stimulation. Morphologically, adipocytes may appear as bloated cells with displaced nuclei and a thin cytoplasmic compartment. An adipocyte may express one or more of the following genes: Adiponectin/Acrp30, FATP4, gAdiponectin/gAcrp30, FATP5, Clathrin Heavy Chain 2/CHC22, Glut4, FABP4/A-FABP, Leptin/OB, FATP1, PPAR gamma/NR1C3, FATP2, or Pref-1/DLK-1/FA1. Unless otherwise indicated, the term adipocyte includes lipoblasts, mature adipocytes, pre-adipocytes and adipogenic stem cells.

"Adipose tissue," as used herein, refers to a tissue comprising adipocytes or fat. Typically, adipose tissue includes body fat, fat depots and/or loose connective tissue with adipocytes. Adipose tissue may include white fat, yellow fat, and/or brown fat. The term adipose tissue also encompasses tissues and components thereof that are obtained by lipoaspirate. The adipose tissue may be unprocessed or processed by the methods, apparatuses, and systems described herein. In addition to adipocytes, adipose tissue may contain multiple regenerative cell types, including stromal cells, endothelial progenitor, stem cells and other precursor cells. The term "adipose tissue" may be used interchangeably with "fat tissue."

"Biocompatible" refers to a material that is substantially nontoxic to cells in the quantities used, and also does not elicit or cause a significant deleterious or untoward effect on the recipient's body at the location used, e.g., an unacceptable immunological or inflammatory reaction.

"Lipoaspirate," as used herein, refers to a mixture comprising adipose tissue and fluid removed from a subject by liposuction. Lipoaspirate may contain tumescent fluid used during a liposuction procedure. Accordingly, lipoaspirate may contain lidocaine (or other local anesthetic) and/or epinephrine (or other related hormone).

"Membrane stabilizing agent (MSA)," as used herein, refers to an agent that stabilizes the membrane of a cell to prevent injury. MSAs include agents that seal and/or stabilize the membrane of cryopreserved cells, e.g., post-thaw, and, consequently, improve the viability of cryopreserved cells post-thaw. MSAs also include agents that prevent injury to adipocytes during the processing of adipose tissue, e.g., during processing of adipose tissue for a fat transplantation procedure. Typically MSAs include a non-ionic polymer, e.g., a non-ionic polyether, that interacts with the phospholipid bilayer of a cell.

"Stem cell," as used herein, refers to any cell that under the proper conditions will give rise to a more differentiated cell. The term "stem cell" encompasses totipotent, pluripotent, multipotent, oligopotent and unipotent stem cells. The term "stem cell" also encompasses cells (e.g., adult somatic cells) that have been reprogrammed such as, e.g., induced pluripotent stem cells (commonly referred to as iPS cells or iPSCs). Non-limiting examples of stem cells include mesenchymal stem cells, hematopoietic stem cells, stromal cells, and adipose-derived stem cells. Stem cells may also be characterized by an ability to be self-renewing, to regenerate a tissue (e.g., adipose tissue), to give rise to further differentiated cells (e.g., adipocytes) and/or to produce colony-forming units in various laboratory systems.

"Subject," as used herein, refers to an individual to whom an agent is to be delivered, e.g., for experimental, diagnostic, and/or therapeutic purposes. Preferred subjects are mammals, e.g., pigs, mice, rats, dogs, cats, primates, or humans. In certain embodiments, the subject is a human. The animal may be a male or female at any stage of development. In certain embodiments, the subject is an experimental animal such as a mouse or rat. A subject under the care of a physician or other health care provider may be referred to as a "patient."

DETAILED DESCRIPTION OF CERTAIN EMBODIMENTS OF THE INVENTION

Figure 1:
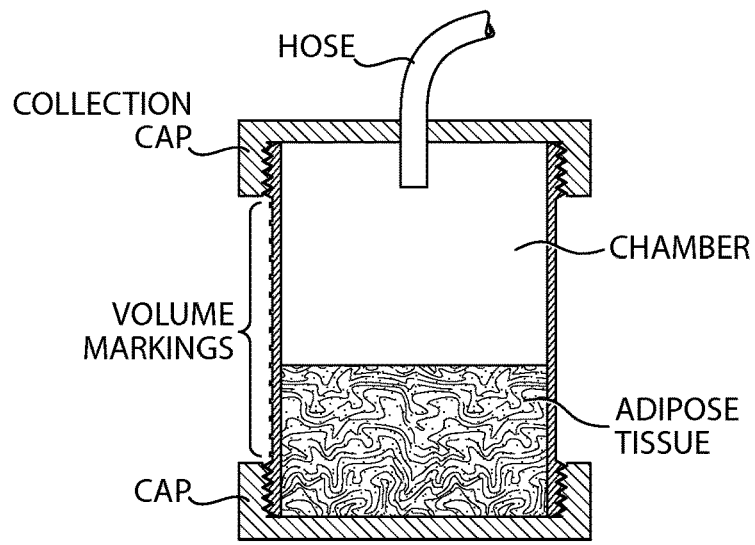
FIG. 1 depicts a non-limiting embodiment of an apparatus for collecting a biological sample, e.g., adipose tissue, for subsequent re-use.

The present invention relates to methods, systems, and apparatuses for improving the quality and/or viability of biological material, such as harvested adipose tissue, lipoaspirate, adipose cells, stem cells, or other cells, tissues, or biological components. Typically, the processed biological material is used for fat transplantation, either for cosmetic, reconstructive, and/or therapeutic purposes. The biological material, for example, may be used in an autologous fat transfer procedure, i.e., where material is taken from the same subject it is later transferred back. In some embodiments, the biological material quality and/or viability is improved by treating the biological material with membrane-repairing/stabilizing agents or the like and/or removal of undesired components of the biological material, such as blood cells, free lipids, excess fluid and/or excess MSA. The biological material may be processed using an inventive system or apparatus comprising one or more stages for removing one or more undesirable components (e.g., free lipids, tumescent fluid, cell debris) from the biological material. It has been discovered that removal of such components improves the quality and/or viability of the biological material, particularly for use as a tissue graft. The present invention further relates to methods, systems, and apparatuses for transplanting the processed biological material, such as adipose tissue. Methods, systems, and apparatuses are provided that control one or more conditions (e.g., pressure, velocity, or shear stress) associated with processing or injection of the biological material (e.g., adipose tissue) in a tissue grafting procedure and result in improved graft quality.

The biological material processed by an apparatus or system of the invention is often lipoaspirate or adipose tissue obtained from a subject. Typically, the processed biological material comprises adipose tissue or a component thereof, including adipocytes, adipogenic cells, mesenchymal cells, and/or stem cells. In general, the processed biological material is biological material from which one or more undesirable components have been removed. The components may be removed by being retained in retention matrix, passing through the filter, being bound by an antigen-binding agent, being scavenged by an antioxidant, or a combination thereof.

Apparatuses for Processing Biological Materials

Apparatuses for processing biological materials are provided in certain aspects of the invention. Such apparatuses are useful for, among other things, processing biological tissue (e.g., adipose tissue) for subsequent re-use. Typically, the apparatuses are sterile and aseptic, and suitable for use in surgical procedures. The chamber and other components of the apparatus are often substantially hermetically sealed to avoid or minimize contamination of the biological material. The inventive apparatuses generally include a chamber for housing a biological material and one or more components for removing undesirable agents or for adding agents (e.g., MSAs) to the biological material. Thus, processing of a biological material can occur through one or more stages within the chamber.

Often the chamber has at least one inlet and at least one outlet. Typically, at least one inlet provides a passage for the biological material to enter the chamber and at least one outlet provides a passage for processed biological material to exit the chamber. A pressure generating device may also be included in, or connected to, the chamber. The pressure generating device is typically configured and arranged for transferring a biological material into the chamber through an inlet, and for discharging a processed biological material out from the chamber through an outlet.

The apparatuses may include a chamber that is cylindrical in shape (having a circular cross-section), although other shapes may be used. The chamber may be provided with a threaded section or other coupling arrangement at either or both ends for affixing various components to the chamber, typically components that facilitate processing of the biological material present within the chamber. Other coupling arrangements that may be used include, e.g., pressure-fit connectors, clamps, or the like. O-rings or other sealing arrangements can also be provided to form a leakproof and/or pressure-resistant seal between each chamber end and an end-piece (e.g., a threaded cap) that is configured to be removably attached to the chamber end. Optionally, such end-pieces may be permanently affixed to an end of the chamber and/or configured to be affixed to other end-pieces. In one configuration, a collector cap may be provided that permits a chamber to function as a collection vessel for a biological material (e.g., lipoaspirate).

The chamber of an inventive apparatus can be provided in any of a range of sizes, depending on the volume of biological material (e.g., adipose tissue) to be extracted, stored, processed, and/or treated therein. For example, the volume of the chamber can range from a few cubic centimeters (cc's) to about 1000 cc's or more, depending on the volume of biological material (e.g., adipose tissue) to be harvested and/or treated. For example, in certain embodiments, the volume of the chamber is about twice to three times the volume of the adipose tissue to be treated. This excess volume allows for the introduction and mixing of membrane-repairing or cell preservation agents with the biological material (e.g., adipose tissue) in the chamber as described herein. The chamber may optionally include volumetric markings to indicate the amount of material contained therein. Such markings can be used to determine the appropriate amount of a solution containing an MSA, cell protectant, or other substance to be added to the adipose tissue for treatment or processing, as described herein. In some configurations, the apparatus comprises multiple chambers, e.g., 1, 2, 3, 4 or more chambers.

The chamber can be provided with any aspect ratio, e.g., height-to-width ratio, length-to-width ratio. For example, the height or length of the chamber may be greater than, less than, or about the same size as the width of the chamber. Different aspect ratios may provide certain advantages in different embodiments. For example, in certain configurations, a chamber that is wider than it is tall (or long) can accommodate a larger filter element for a particular volume of biological tissue to be processed in the chamber. In certain configurations, the chamber may have an aspect ratio (height-to-width or length-to-width) of 1:1, 2:1, 3:1, 4:1, 5:1, or 10:1. The chamber may have a cross-sectional inner diameter in a range of 0.5 cm to 1 cm, 0.5 cm to 2 cm, 0.5 cm to 5 cm, 1 cm to 2 cm, 1 cm to 5 cm, 1 cm to 10 cm, or more. The chamber may have a cross-sectional inner diameter of about 0.5 cm, about 1 cm, about 2 cm, about 3 cm, about 4 cm, about 5 cm, about 6 cm, about 7 cm, about 8 cm, about 9 cm, about 10 cm, or more. The chamber may have a length in a range of 1 cm to 5 cm, 2 cm to 5 cm, 2 cm to 10 cm, 5 cm to 10 cm, 5 cm to 20 cm, 5 cm to 30 cm, or more. The chamber may have a length of about 1 cm, about 2 cm, about 3 cm, about 4 cm, about 5 cm, about 6 cm, about 7 cm, about 8 cm, about 9 cm, about 10 cm, about 15 cm, about 20 cm, about 25 cm, about 30 cm, or more.

In certain configurations, a biological material (e.g., adipose tissue or a component thereof, such as adipose cells (adipocytes)) is maintained within a single chamber while being processed and each end of the chamber is provided with a threaded coupling or other attachment arrangement for affixing various end-pieces thereto. For example, the chamber may be provided with an end-piece in the form of an impermeable cap on a distal end to form a container. Harvested adipose tissue can be placed in the chamber for further processing using any appropriate technique. In certain configurations, a collection cap that includes a hose or tube is affixed to a proximal end of the chamber. The collection cap is in communication with, e.g., a liposuction hose, such that a biological material (e.g., lipoaspirate) is directed into the chamber while being harvested. Reducing or eliminating the need to transfer the biological material between multiple vessels or containers reduces the amount of mechanical damage incurred, increases the efficiency of the process, reduces the loss of material, and/or reduces the likelihood of contamination.

The chamber of an inventive apparatus may be configured to be used in a centrifuge. In certain configurations, fractions of a biological material in the chamber that are segregated by centrifugation (e.g., oil, infranatant) can be readily removed from the chamber. End-pieces (e.g., solid caps) may be affixed to one or both ends of a chamber, such that the chamber may be placed in a centrifuge and spun to separate fractions of a biological material present in the chamber. After segregation of fractions of a biological material by centrifugation, an end-piece containing a filter arrangement, retention matrix or other device can be affixed to an end of the chamber having segregated components, such as, for example, fluids or free lipids. An end-piece that includes a pressure-delivery arrangement (e.g., a plunger or a gas hose) can be affixed to another end of the chamber where it can be employed (e.g., the plunger can be depressed or the gas hose can be pressurized) to drive the segregated fractions into the filter, retention matrix or other device.

An end-piece may be provided that includes a container configured to be attachable to the chamber, and a further plunger at a distal end of the container. The further plunger can be configured to vary the effective volume within the chamber when the plunger is translated. The further plunger can be formed as part of the chamber, or it can be provided as a removable end-piece that can be affixed to an end of the chamber.

Filters

Apparatuses of the present invention can be used to remove impurities from adipose tissue or other biological material placed in the chamber using mechanical filtration and/or other processes. Impurities can include, for example, excess fluids, free lipids, blood cells, cell debris, extracellular material, and excess quantities of certain agents or solutions that may be added to the biological tissue or material to achieve certain effects. To facilitate removal of such impurities, the apparatuses typically comprise at least one filter. The filter is configured and arranged for contacting the biological material, when present in the chamber of an apparatus, such that a waste fraction of the biological material passes through the filter. At least one outlet of the chamber is generally configured and arranged to permit discharge from the chamber of biological material that does not pass through the filter. Multiple filters may be provided to permit filtering of the biological material in stages. The apparatus may include 1 filter, 2 filters, 3 filters, 4 filters, 5 filters or more.

Often at least one waste outlet line is provided that is fluidically connected with the chamber such that the waste fraction exiting the filter (the filtrate) discharges through the waste outlet line. In some cases, the waste outlet line is configured and arranged to permit flow into the chamber through the filter to facilitate cleaning of the filter. By allowing for reverse-flow, material that has been lodged in the filter, which results in clogging of the filter, can be removed. This allows for cleaning of the filter without disassembly of the chamber. Although, in some cases, the filter may be cleaned by removing it from the chamber and washing it. Thus, in some configurations the filter is removable and replaceable.

The filter may have any of a variety of shapes and sizes. The filter may shaped as a disc, an annular ring, a cylinder, a hollow cylinder, a sheet, etc. The filter may have an effective pore size in a range of about 1 μm to about 5 mm, about 1 μm to about 1 mm, about 1 μm to about 100 μm, about 1 μm to about 50 μm, about 10 μm to about 50 μm, about 20 μm to about 50 μm, about 50 μm to about 500 μm, about 100 μm to about 500 μm, or about 100 μm to about 1 mm. The filter may have an effective pore size of about 1 μm, about 5 μm, about 10 μm, about 20 μm, about 50 μm, about 100 μm, about 250 μm, about 500 μm, about 1 mm, about 2.5 mm, about 5 mm, or more.

The filter may have an effective pore size that is relatively homogeneous throughout the filter. Alternatively, the filter may have an effective pore size that is position-dependent. For example, the filter may have an effective pore size at a position upstream in the chamber that is relatively coarse, and an effective pore size at a position downstream in the chamber that is relatively fine. Thus, upstream relatively large impurities in the biological material may pass through the filter and downstream only relatively fine impurities in the biological material may pass through the filter. For example, the filter may have an effective pore size at a position upstream in the chamber that is in a range of about 50 μm to about 100 μm, and an effective pore size at a position downstream in the chamber that is in a range of about 1 μm to about 50 μm.

In certain embodiments in which adipose tissue is the biological material, the filter characteristics are selected to retain adipose cells in the chamber and allow liquids and smaller impurities to pass through the filter when pressure is applied to the adipose tissue in the chamber. For example, the size of a typical adipose cell is between about 60 and about 100 microns. Accordingly, in certain embodiments, the effective size of the pores or passages in the filter are between about 20 microns and about 50 microns. Such pore sizes allow liquids and small impurities, such as blood cells, to pass through the filter and be removed from the adipose tissue while retaining the adipose cells and globules of adipose tissue in the chamber. Filters having other effective pore sizes may also be used based on the relative sizes of adipose cells and particular impurities or agents to be removed, where the pore size is preferably smaller than the average or minimum adipose cell size and larger than the size of the impurities to be removed.

The filter may be composed of any one or more of a variety of different biocompatible materials. For example, the filter may be composed of one or more of a ceramic, glass, silicon, stainless steel, a cobalt-chromium alloy, a titanium alloy, polytetrafluoroethylene, polypropylene, and other polymers. The filter may also be coated with a material to prevent or minimize sticking of components present in the biological material to the filter, which could lead to clogging of the filter.

Typically, at least one outlet of the chamber is configured and arranged to permit discharge from the chamber of the waste fraction of the biological material following exit from the filter. When the biological material is a lipoaspirate, the waste comprises at least one of lipids, blood components, tumescent fluid, individual cells, and cellular debris.

Filters or agents that are coated or treated with adsorbent materials may also be provided to remove impurities. For example, a lipophilic substance can be provided to adsorb free lipids, or excess MSAs or cell protectants that are lipophilic, if used, from the adipose tissue. Such adsorbent agents can be provided in a filter. The adsorbent materials or agents can be used instead of or in addition to absorbent materials as described herein. Exemplary adsorbent and/or absorbent agents that may be used in accordance with embodiments of the present invention include, but are not limited to, hydrogels such as polysaccharides (e.g., agarose or carboxymethylcellulose), cross-linked PEGs, polyvinyl alcohols or co-polymers thereof, polyacrylamides, polyacrylonitriles, polyacrylates, and/or co-polymers thereof.

Pressure Generating Devices

As disclosed herein, one or more pressure generating devices may be included in, or connected to, the chamber of an inventive biological material processing apparatus. Pressure generating devices are typically configured and arranged for transferring a biological material into the chamber through an inlet, and/or for discharging a processed biological material out from the chamber through an outlet.

In some configurations, a pressure generating device is a pump. The pump may be configured and arranged for transferring the biological material into the chamber and discharging the biological material through the outlet. The apparatus, in these configurations, typically also includes a controller configured and arranged for generating control signals that activate the pump to generate the positive pressure. The apparatus may also include a pressure sensor that is fluidically connected to the chamber and that includes an electrical output connected to an input of the controller. The pressure sensor provides an electrical signal to the controller indicative of a sensed pressure in the chamber. The controller transmits control signals to the pump based on the sensed pressure.

In certain configurations, an end-piece for a chamber includes a hand-operated plunger mechanism that functions as a pressure generating device. The plunger mechanism may include a rod affixed to a piston body, in which the perimeter of the piston body substantially conforms to the inner surface of the chamber, similar to the structure of a conventional syringe. Pressing down on the plunger increases the pressure in the chamber, and pulling up on the plunger reduces the pressure in the chamber. If one or more openings are provided on the lower end of the chamber, as described herein, pressing down or pulling up on the plunger forces material out from or pulls material into the chamber, respectively. Pressure from the plunger may be used to force impurities (e.g., extracellular fluid, proteins, lipids, nucleic acids, red blood cells) through a filter while retaining other components of the biological material (e.g., larger adipose cells or fat globules in the chamber).

In some configurations, a force-limiting plunger arrangement is used. This plunger arrangement includes a rod configured to fit into an opening that extends at least partially along a longitudinal axis of a sleeve. A piston body is affixed to a distal end of the sleeve, or it may be formed as an integral part of the sleeve. The rod and sleeve may have circular cross-section shapes, or other cross-sectional shapes may be used (e.g., hexagonal, octagonal, square, or triangular shapes). A clutch arrangement, e.g., a frictional interface, can be provided between the outer surface of the rod and the inner surface in the sleeve when the rod is inserted partially into the sleeve. In operation, pushing down on the rod with a relatively small force will allow the rod to frictionally grip the surrounding portion of the sleeve and transmit the force to the piston body. This operation can be similar to that of a conventional syringe, where applying force to the proximal end of the plunger causes the piston body to press onto any substance provided in the chamber. However, if the force applied to the rod exceeds a predetermined limit, the frictional interface may be configured to allow the rod to slip relative to the sleeve, such that the rod enters the sleeve further and no additional force is transmitted to the piston body. In this manner, the amount of force conveyed to the piston head—and thus the pressure applied to a material in the chamber to which the plunger is attached—is limited. This limiting force or pressure value can be determined based on characteristics of the frictional interface between the rod and the sleeve and the size of the piston body. In this manner, a simple force-limiting "clutch" mechanism can be provided in the plunger arrangement to prevent application of excessive force or pressure using the plunger. The desired maximum force or pressure is typically selected to avoid or lessen the likelihood of causing damage to adipose cells or other cells in the chamber when the plunger is pressed down, e.g., to force some impurities through a filter at the distal end of the chamber.

In certain configurations, a filter arrangement may be affixed to the distal end of the chamber, optionally with a waste cup. A controlled pressure source, such as a pressurized gas (e.g., air, $N_2$) with a pressure regulator, may be provided in communication with the hose of the collector cap. In this manner, the pressurized gas is used to controllably increase the pressure within the chamber and facilitate expulsion of impurities through the filter, while avoiding application of excessive pressure that can damage adipose cells. In further embodiments, the gas can include components, such as oxygen, that may further improve the viability of the adipose cells being treated.

In a further embodiment, an end-piece is provided for the chamber that includes a filter or barrier that is arranged to provide an osmotic gradient across the filter/barrier, such that fluid flows from the chamber to a waste cup or vice-versa in response to an osmotic pressure gradient, instead of or in addition to mechanical pressure.

Retention Matrices

Typically, the chamber houses one or more retention matrices that are configured and arranged for contacting the biological material, when present in the chamber, such that a fraction of the biological material is retained in the retention matrix. Retention matrices are generally composed of one or more materials that retain components from the biological material. In this way, a retention matrix provides a mechanism for removing one or more undesirable components from the biological material. Typically, at least one outlet of the chamber is configured and arranged to permit discharge from the chamber of biological material that is not retained in the retention matrix.

A retention matrix may be composed of a lipophilic matrix (or hydrophobic matrix) that retains lipids from the biological material. Retention of the lipid fraction may occur through adsorption of lipids to the lipophilic matrix, absorption of the lipid fraction into the lipophilic matrix, or a combination of such retention mechanisms, depending on the nature of the matrix and composition of the lipids present in the biological material. For example, certain lipids may adsorb to the matrix; whereas certain other lipids may be absorbed by the matrix. Some lipids may be retained by both adsorption and absorption. The lipids may comprise free lipids, phospholipids, sterols, fat-soluble vitamins, fatty acids, monoglycerides, diglycerides, triglycerides, or any other lipid components present or commonly found in biological materials, such as adipose tissue. Additive components (e.g., excess additives) (which may or may not be lipids themselves) may also adsorb to or be absorbed by a lipophilic matrix. In some examples, the lipophilic matrix comprises a polysaccharide, a cross-linked polyethylene glycol, a polyvinyl alcohol or co-polymer thereof, a polyacrylamide, a polyacrylonitrile, a polyacrylate, or a co-polymer thereof.

The retention matrix may be composed of a hydrophilic matrix that absorbs and retains water from the biological material. Thus, the hydrophilic matrix may function as a hydrogel. The hydrophilic matrix may comprise a non-toxic osomotic material. The hydrophilic matrix may comprises a hyaluronic acid, a carbohydrate, gelatin, alginate, methyl cellulose, or hydroxymethyl cellulose.

The retention characteristics of the retention matrix may be position-dependent in the chamber. For example, the retention matrix may be lipophilic at a position upstream in the chamber and hydrophilic at a position downstream in the chamber. Alternatively, the retention matrix may be hydrophilic at a position upstream in the chamber and lipophilic (e.g., hydrophobic) at a position downstream in the chamber. In this way, a retention matrix is capable of retaining different types of components from the biological matrix. In some cases, the retention matrix may comprise a relatively homogenous distribution of different retention regions, e.g., a homogeneous distribution of lipophilic and hydrophilic regions. Multiple retention matrices may be present in different positions within the chamber. The retention matrices may retain different components of the biological material including, for example, $H_2O$, lipids, metals, MSA, blood cells.

The entire apparatus or chamber may be disposable, including the retention matrix and other components of the chamber. In some cases, the chamber and system are arranged and configured to be readily disassembled into one or more component parts. In this way, the system may be readily cleaned and components of the system may be readily replaced or reassembled following cleaning. Accordingly, the retention matrix can be an integral component of the chamber that is not readily removable. Alternatively, the retention matrix may be readily removable and replaceable.

Through the use of retention matrices, impurities, including excess MSA or cell protectant if used, may be removed from adipose tissue in the chamber. This may be accomplished, for example, by contacting an absorbent material and/or adsorbent material of a retention matrix with the adipose tissue. For example, a water-absorbent material (e.g., hydrogel) can be provided in a retaining cap that can be affixed to one end of the chamber as shown. The chamber can then sit for a time interval or be gently shaken or agitated to provide sufficient contact between the adipose tissue and the absorbent material. After such contact has occurred for a sufficient time, e.g., up to 5 minutes, up to 1 minute, the retaining cap with the absorbent material can be removed from the chamber, along with any absorbed water or other impurities that are present in the absorbing material. After this process, there will be fewer impurities remaining with the adipose cells in the chamber.

In certain embodiments, an enclosure housing a retention matrix can be affixed to an end of the chamber to form a larger enclosure for retaining impurities of the biological material. A filter may be used together with the retention matrix. The filter and retention matrix may optionally by provided as separate end-pieces that may be affixed to one another and to the chamber, or they may be provided as a single end-piece that is affixed to the chamber. The biological material with impurities (including any MSA or cell protectant, if used) may then be contacted with the retention matrix, e.g., by inverting the chamber/absorbent enclosure assembly. A relatively large surface area of the retention matrix provides improved contact between the biological material and the absorbent material to facilitate better absorption of impurities.

The chamber may also include one or more antigen-binding agents for binding and sequestering target antigens present in the biological material. The antigen-binding agents are typically immobilized on a solid support. In some configurations, the antigen-binding agent is immobilized on a retention matrix (e.g., a lipophilic matrix or hydrophilic matrix). In other configurations, the anti-binding agent is immobilized on a separate structure (e.g., a surface of the chamber) or matrix. The antigen-binding agent may bind specifically to a cell surface molecule, extracellular matrix molecule, or other target. The cell surface molecule may be present on a red blood cell, white blood cell, platelet, stromal cell, bacterium, virus, or other target. In general, the target of the antigen-binding agent is an undesirable component of the biological material. The antigen-binding agent is generally an antibody, or antigen binding fragment thereof.

The chamber may also include one or more antioxidants for scavenging free radicals in the biological material. The antioxidants may be immobilized on a solid support in the chamber. In some configurations, the antioxidant is immobilized on a retention matrix (e.g., a lipophilic matrix or hydrophilic matrix). In other configurations, the antioxidant is immobilized on a separate structure (e.g., a surface of the chamber) or matrix. Examples of antioxidants useful in the present invention include, but are not limited to, glutathione, vitamin C, vitamin E, or an enzyme, such as a catalase, a superoxide dismutase, or a peroxidase.

Additive Reservoir

The system may also comprise a reservoir configured and arranged for housing an additive solution. The additive solution may comprise a membrane stabilization agent (MSA), a growth factor, an antioxidant, or other appropriate additive disclosed herein or otherwise known in the art. The MSA may be a tri-block co-polymer of the form: polyethylene glycol-polypropylene glycol-polyethylene glycol, such as Poloxamer-P188. The reservoir is typically configured and arranged to permit transfer of the additive solution from the reservoir to the biological material prior to the biological material contacting the retention matrix. However, the reservoir may be configured and arranged to permit transfer of the additive solution to the biological material at any stage of processing in the chamber. Typically, the additive solution is transferred from the reservoir to the chamber using a pump or other similar device. In some cases, the retention matrix is configured and arranged to retain an excess of one or more components of the additive solution by adsorption or absorption.

Damage to the harvested cells (e.g., adipocytes or the like), if present, can be repaired or prevented by mixing the adipose tissue with a membrane stabilization agent (MSA) or cell protectant, such as, e.g., Poloxamer P188 or lipoic acid. MSAs or cell protectants that may be used to improve the viability of cells are described, e.g., in International Application No. PCT/US2009/005727, filed Oct. 21, 2009 and U.S. Patent Application Publication No. 2010/0104542. The MSA or cell protectant can be introduced into the chamber in various ways. For example, the MSA or cell protectant can be provided in a solution that is either pre-loaded in the chamber or added to a solution container in communication with the chamber. Certain MSAs or cell protectants may also be provided, e.g., in the form of a solid such as a powder, or in liquid form (i.e., not in solution). The MSA or cell protectant is preferably sterile to avoid contamination of the cells or tissue being treated.

In certain embodiments, a cap is provided on the proximal end of the chamber to facilitate mixing of the MSA or cell protectant with the biological material. The MSA or cell protectant solution may be introduced into the chamber and mixed with the biological material therein by inverting the chamber/solution container assembly, such that the MSA or cell protectant solution passes through the filter and into the chamber. Alternatively, a plunger mechanism may be affixed to the proximal end of the chamber, such that the plunger may be partially withdrawn from the chamber to draw the MSA or cell protectant solution through the filter and into the chamber. Other techniques can also be used to introduce the MSA or cell protectant solution into the chamber. For example, an end-piece provided at one end of the chamber can be removed, and a particular amount of the MSA or cell protectant solution can be poured into the chamber.

The MSA or cell protectant solution can be provided in a pre-measured amount. For example, if P188 is used as the MSA, it can be provided in a 10 mg/ml aqueous solution (e.g., a PBS solution or other buffered solution comprising the MSA) with the volume of solution used being approximately the same as the volume of adipose tissue to be treated. The mixture of adipose tissue and MSA or cell protectant solution in the chamber can be gently shaken, subsequent mixing by inversion, swirling, etc. and/or allowed to sit for a duration sufficient to allow the MSA or cell protectant to interact with the cells. For example, the mixture can be allowed to sit for about 1 minute, about 5 minutes, about 10 minutes, about 20 minutes or longer. Shorter time durations may be used. In some cases, the mixture is shaken to improve mixing of cells in the biological material and the MSA or cell protectant.

In certain embodiments, the MSA, cell protectant, and/or other treatment/processing substance is provided at a temperature below normal body temperature and/or below ambient temperature ("room temperature"). Alternatively or additionally, the chamber containing the cells is cooled before and/or after introduction of the adipose tissue or other cells. Such cooler temperatures can further facilitate preservation and viability of the cells or tissue being processed.

After the adipose tissue has been sufficiently mixed and/or exposed to the MSA or cell protectant, the MSA or cell protectant is optionally removed from biological materaial. Other materials in addition to or instead of MSAs or cell protectants, e.g., any substance that can produce a beneficial effect on the cells or other biological material in the chamber, can also be used as described herein. Such materials and/or further cell protectants or MSAs may be used in combination or may be used to sequentially treat the harvested cells or tissue, in accordance with the inventive apparatuses and techniques described herein.

Agitation

The system may be further provided with an agitation device configured and arranged for agitating the biological material while present in the chamber. In some configurations, agitation of the biological material either in the chamber or prior to entering the chamber facilitates movement of the biological material into and out of the chamber, as well as contacting of the biological material with retention matrices, filters, and other components of the chamber to facilitate removal of one or more undesirable components of the biological material. The agitation device may be an internal stirring or mixing mechanism that is in direct or indirect contact with the biological material. The agitation device may also be an external device such as a vibratory device, shaker-table, or other similar device suitable for agitating the biological material externally.

Methods for Processing Biological Materials

Methods for processing biological materials are provided herein. The methods are particularly useful for fat transplantation procedures. For example, lipoaspirate obtained from a subject may be processed using the methods and to produce adipose tissue suitable for transplantation into the subject for cosmetic or reconstructive purposes. The methods, which are often used for preparing tissue grafts, typically involve obtaining an appropriate apparatus as disclosed herein; obtaining a biological material (typically from a subject); and causing the pressure generating device of the apparatus to transfer the biological material into the chamber of the apparatus through the chamber inlet and to discharge processed biological material out from the chamber through the chamber outlet. In some configurations, the pressure generating device is not required for loading the biological material into the device. In these configurations, the biological material may be manually added (e.g., poured) into the chamber. The pressure generating device in this configuration would facilitate movement of the biological material through the one or more processing stages of the apparatus and optionally discharge the processed biological material through the outlet.

In certain embodiments, the lipoaspirate is subjected to centrifugation prior to ordinary processing using the apparatus. In some cases, after centrifugation, an oil layer and/or infranatant layer is removed from the lipoaspirate In some configurations of the apparatuses, any combination of end-pieces and procedures described herein can be used to collect, treat and/or process the biological materials (e.g., adipose tissue). Individual procedures may also be performed in different orders and/or more than one, such as using a plurality of absorbent caps with fresh absorbent materials. The type and number of processes to use can be based on various factors such as the amount of adipose tissue being treated, the desired purification level of the adipose cells, the extent of membrane repair or other treatment of the adipose cells that is desired or selected, the site from which the cells or tissue were extracted, the site of transplantation, etc.

After the adipose tissue has been treated using any of the various procedures and devices described herein, an end-piece that includes a needle, catheter, cannula, or other suitable opening can be affixed to a distal end of the chamber for delivery of the processed biological material to a subject. The needle, catheter, cannula, or other suitable opening can be used to facilitate transplantation of the treated adipose tissue into one or more particular locations in a patient's body. For example, a plunger mechanism can be affixed to the proximal end of the chamber and used to force the treated and/or processed adipose cells through the needle, catheter, cannula, or other suitable opening. In this manner, the harvested adipose tissue can be treated and transplanted using a single chamber, which can reduce the amount of damage to the adipose cells and improve their overall viability.

Apparatuses for Injecting, Transplanting, or Transferring Biological Materials

Apparatuses are provided for injecting, transplanting, or transferring biological materials under conditions that result in improved quality, consistency and viability of the biological material for grafting purposes compared with existing apparatuses. The apparatus typically comprises a chamber having at least one outlet; and a pressure generating device configured and arranged for generating a positive pressure within the chamber that is at or below a predetermined threshold, the positive pressure being sufficient to cause a biological material, if present in the chamber, to be discharged through the outlet. The apparatus may include a pressure sensor configured and arranged for measuring pressure within the chamber.

Generally, the predetermined threshold is a pressure above which the biological material has relatively low viability as a tissue graft following discharge from the outlet into a graft site in a subject. The extent of viability may be compared with a control graft sample having a desired set of viability conditions, or a historical value or values representing a desired set of viability conditions. Viability may be assessed using methods well known in the art. For example, viability may be assessed by evaluating the extent of graft retention (e.g., by thickness, by volume, adipocyte content, cell viability, or other lack of inflammation parameter) and/or growth following transplantation at one or more times following transplantation. Graft viability may be assessed qualitatively by evaluating the aesthetic appearance of a subject who has received a fat graft. Clinically, graft viability can also be assessed using MRI, or 3D imaging volume measurements. Prior to grafting fat viability can be measured using an automated cell counter. Again, the assessment may be performed at one or more times following the graft. For example, if the graft was made to reduce or eliminate one or more facial wrinkles, the maintenance of a reduction or apparent absence of the wrinkles at one or more points in time following the graft may be indicative of sufficient viability. Thickness of a graft and quality may also be assessed by other more quantitative methods such as by using ultrasound or other means to determine the quality of a graft over time in a subject. The skilled artisan will be familiar with other approaches that may be used for evaluating graft viability.

The predetermined threshold may be about 2 atm, about 3 atm, about 4 atm, about 5 atm, about 6 atm, or more. The predetermined threshold may be in a range of about 2 atm to about 3 atm, about 3 atm to about 4 atm, about 2 atm to about 5 atm, about 2 atm to about 6 atm, or about 4 atm to about 6 atm. Often the predetermined threshold is a pressure above which the velocity of the biological material discharging from the outlet exceeds a predetermined maximum. For example, the predetermined maximum may be about 5 cm/sec, about 10 cm/sec, about 20 cm/sec, about 30 cm/sec, about 40 cm/sec, about 50 cm/sec, about 60 cm/sec, about 70 cm/sec, about 80 cm/sec, about 90 cm/sec, about 100 cm/sec, about 150 cm/sec, about 200 cm/sec, about 250 cm/sec, or more. The predetermined maximum may be in the range of about 5 cm/sec to about 20 cm/sec, about 10 cm/sec to about 50 cm/sec, about 20 cm/sec to about 100 cm/sec, about 50 cm/sec to about 200 cm/sec, about 50 cm/sec to about 250 cm/sec, or more. The predetermined maximum may be about 265 cm/sec. The positive pressure is often maintained such that the velocity of the biological material being discharged from the outlet is in a range of about 5 cm/sec to about 265 cm/sec.

In some configurations, the outlet is positioned at a distal end of the chamber, the chamber comprises an opening at a proximal end, and the pressure generating device is a plunger arrangement configured and arranged to pass through the opening at the proximal end and to be movably disposed in the chamber, such that displacement of the plunger arrangement within the chamber toward the distal end generates the positive pressure necessary to discharge the material in the chamber. The plunger arrangement, in some configurations, may be advanced into the chamber by depressing the plunger arrangement (e.g., by hand). The plunger arrangement may also be operated automatically using an electric motor, for example, that is coupled to the plunger arrangement such that rotation of the motor causes the plunger arrangement to advance into or out from the chamber. Operation of the motor may be controlled automatically based on a sensed pressure in the chamber in order to ensure that the pressure in the chamber does not exceed the predetermined threshold.

In some configurations, the plunger arrangement comprises a force-limiting clutch arrangement that couples a rod to a piston. The force-limiting clutch arrangement may comprise a frictional interface mechanically coupling the rod to the piston. The force-limiting clutch arrangement may be configured and arranged to limit, to the predetermined threshold, the maximum pressure developed in the chamber by depressing the rod of the plunger arrangement toward the distal end.

The arrangement may comprise a plunger displacement device (e.g., an electric motor, compressed air drive, vacuum drive) configured and arranged for displacing the plunger arrangement toward the distal end. The plunger displacement device may be configured and arranged for displacing the plunger arrangement toward the distal end at a predetermined rate. The predetermined rate may be a rate of displacement of the plunger arrangement that results in a positive pressure in the chamber at or below the predetermined threshold while discharging the biological material from the outlet. The apparatus may also include a controller configured and arranged for generating control signals that activate the plunger displacement device to displace the plunger arrangement toward the distal end. The apparatus may also include a pressure sensor that is fluidically connected to the chamber and that includes an electrical output connected to an input of the controller, such that the pressure sensor provides an electrical signal to the controller indicative of a sensed pressure in the chamber, in which the controller transmits control signals to the plunger displacement device based on the sensed pressure.

In some configurations, the pressure generating device for injecting the processed biological material is a pump. The pump may be configured and arranged for transferring the biological material into the chamber and discharging the biological material through the outlet. The apparatus, in these configurations, typically also includes a controller configured and arranged for generating control signals that activate the pump to generate the positive pressure. The apparatus may also include a pressure sensor that is fluidically connected to the chamber and that includes an electrical output connected to an input of the controller, the pressure sensor providing an electrical signal to the controller indicative of a sensed pressure in the chamber, in which the controller transmits control signals to the pump based on the sensed pressure.

In some configurations, the output of the chamber is fluidically connected with a cannula (e.g., a blunt cannula) or catheter. While any appropriate size may be used, the cannula or catheter is typically, 12, 14, 15, 16, 17, or 18 gauge.

The chamber is generally configured and arranged to contain 1 ml to 1 L of the biological material. However, a range of volumetric sizes may be constructed. In some configurations, the chamber is configured and arranged to contain a volume of the biological material in the range of 1 ml to 1 L, 1 ml to 500 ml, 1 ml to 100 ml, 1 ml to 50 ml, 50 ml to 100 ml, 20 ml to 100 ml, or 0.5 ml to 1 ml.

Methods for transplanting processed biological material, e.g., adipose tissue for autologous fat grafting, are also provided. Typically, the methods involve obtaining processed biological material according to any of the methods disclosed herein; and transplanting the processed biological material into a subject. Methods for injecting, transplanting or transferring biological materials may include obtaining any one of the apparatuses disclosed herein; loading the biological material into the chamber of the apparatus; and causing the pressure generating device of the apparatus to generate the positive pressure within the chamber that is at or below the predetermined threshold to cause the biological material to discharge through the outlet. Often pressure in the chamber is monitored during the transplantation to ensure that the pressure does not exceed the predetermined threshold.

Typically, the methods involve obtaining processed biological material according to any of the methods disclosed herein; and transplanting the processed biological material into a subject. For fat transfer (grafting) procedures, the processed biological material generally comprises adipose tissue or one or more components thereof. In autologous fat transfer procedures, the adipose tissue is obtained, typically as lipoaspirate, from the subject; it is then processed and injected back into the patient at a new location. The biological material may be obtained by extraction of adipose tissue from the abdomen, thigh, flank region, or gluteal region of the subject or by extraction of lipoaspirate comprising such adipose tissue of the subject. For cosmetic purposes, the processed biological material is often transplanted under the skin of a nasolabial fold, lip, nasojugal region, malar, chin, forehead, lower eyelid, or upper eyelid of the subject.

Although the exemplary methods and apparatus disclosed herein are described mostly with respect to treating or processing adipose tissue (e.g., harvested fat), they may be used with any biological material that benefits from any of the exemplary processing procedures described herein. Such procedures include, for example, removal of impurities or certain components by filtering and/or absorption/adsorption. The biological material (e.g., adipose tissue or other tissue) can be combined with any substance that may produce a beneficial or desirable effect in the biological material, in addition to the MSAs or cell protectants described herein. Excess substance can also be removed after combining it with the biological material using the exemplary apparatus and methods described herein.

Kits

The apparatuses and systems described herein can be provided as a kit for treating harvested adipose tissue, lipoaspirate, or other biological material. The kit can include one or more chambers that can be disposable and/or sterilizable. Such chambers can be provided in various sizes/volumes as described herein. A variety of end-pieces can be provided that can be affixed to an end of the chambers. Such end-pieces may include collection caps, filters, waste cups, caps, or containers provided with absorbent or adsorbent materials or agents, plunger mechanisms, needles or cannulas, etc Such end-pieces can be provided in different sizes that are configured to be affixed to different-sized chambers. A quantity of one or more MSAs or other agents for treating or processing the biological material may also be provided. Such agents may be provided in a liquid form, e.g., as a pure liquid, suspension, solution or emulsion, or as a crystalline or powdered solid, or even in gaseous form. Such substance(s) can be provided in a dispensing bottle or container, or in one or more containers that can be configured to be affixed to the chamber that holds the adipose tissue or other biological material. The substance (e.g., an MSA or cell protectant) can be provided in such containers in pre-measured volumes for use with appropriate volumes of harvested adipose tissue, etc.

The foregoing merely illustrates the principles of the invention. Various modifications and combinations of the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. Exemplary embodiments of the invention will be described in more detail by the following examples. These embodiments are exemplary of the invention, which one skilled in the art will recognize is not limited to the exemplary embodiments.

All references described herein are incorporated by reference for the purposes described herein.

EXAMPLES

Example 1: An Apparatus for Collecting a Biological Sample, e.g., Adipose Tissue, for Subsequent Re-Use FIG. 1 depicts an apparatus for collecting a biological sample, e.g., adipose tissue, for subsequent re-use. The apparatus includes a chamber that is cylindrical in shape. The chamber is provided with a threaded section. However, other coupling arrangements may be used at either or both ends. Other coupling arrangements that may be used include, e.g., pressure-fit connectors, clamps, or the like. O-rings or other sealing arrangements can also be provided to form a leakproof and/or pressure-resistant seal between each chamber end and an end-piece that is configured to be removably attached thereto. Optionally, such end-pieces may be permanently affixed to an end of the chamber and/or configured to be affixed to other end-pieces. The chamber may optionally include volumetric markings to indicate the amount of material contained therein, as shown in FIG. 1. In this example, adipose cells (adipocytes) are maintained within a single chamber while being processed. Each end of the chambers is provided with a threaded coupling or other attachment arrangement for affixing various end-pieces thereto. For example, as shown in FIG. 1, the chamber can be provided with an end-piece in the form of an impermeable cap on the distal end to form a container. Harvested adipose tissue can be placed in the chamber for further processing using any appropriate technique. In certain embodiments, a collection cap that includes a hose or tube is affixed to the proximal end of the chamber, as shown in FIG. 1.

Example 2: A Filter Apparatus with a Hand-Operated Plunger Arrangement

Figure 2:
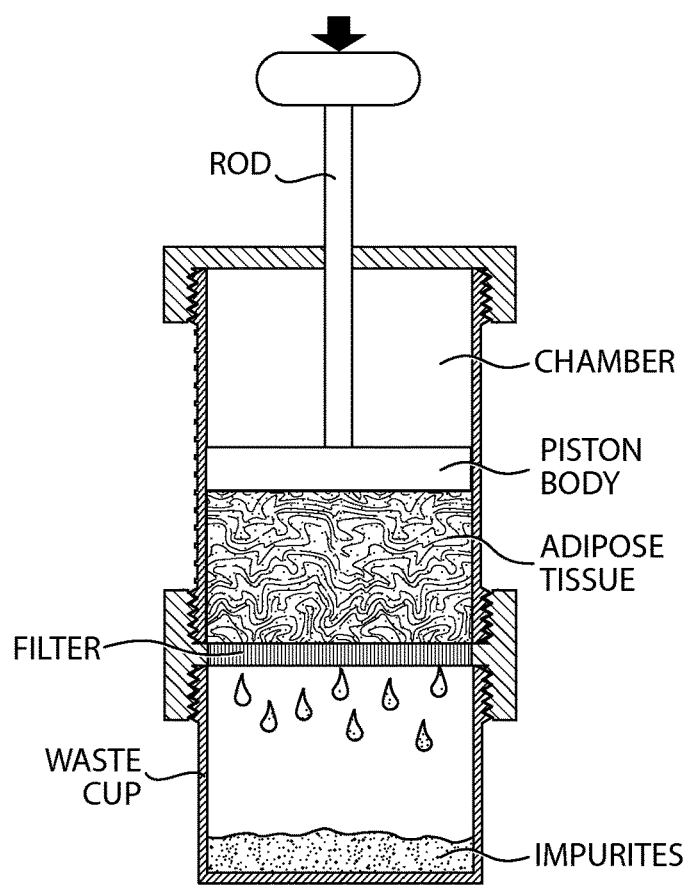
FIG. 2 depicts a non-limiting embodiment of a filter apparatus with a hand-operated plunger arrangement.

In another example, a filter, as shown in FIG. 2, can be affixed to the distal end of the chamber depicted in FIG. 1. For example, the collection cap as shown in FIG. 1, if used, is removed, and a plunger mechanism is affixed to the proximal end of the chamber. The chamber is then inverted, such that the distal end of the chamber is on top, and the filter arrangement is affixed to the distal end of the chamber. In certain embodiments, a waste cup is affixed to the chamber, as shown in FIG. 2, or the filter arrangement and waste cup are provided as a single component. An end-piece that includes a hand-operated plunger mechanism is affixed to the proximal end of the chamber.

Example 3: A Plunger Arrangement with a Frictional Interface

Figure 3:
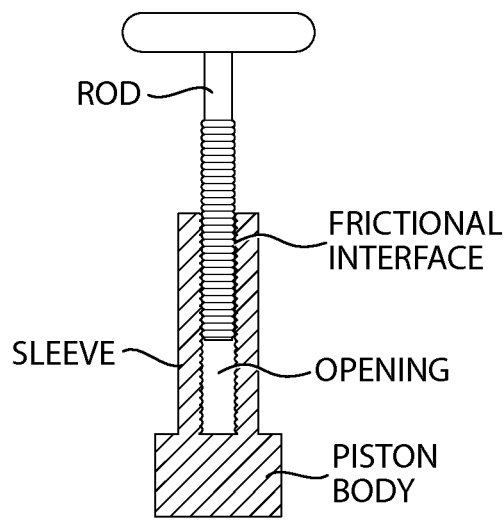
FIG. 3 depicts a non-limiting embodiment of a plunger arrangement with a frictional interface.

An exemplary force-limiting plunger arrangement that may be used with certain embodiments of the present invention is shown in FIG. 3. This plunger arrangement includes a rod configured to fit into an opening that extends at least partially along a longitudinal axis of a sleeve. A piston body is affixed to a distal end of the sleeve, or it may be formed as an integral part of the sleeve. The rod and sleeve may have circular cross-section shapes, or other cross-sectional shapes may be used (e.g., hexagonal, octagonal, square, or triangular shapes).

A clutch arrangement, e.g., a frictional interface or the like, can be provided between the outer surface of the rod and the inner surface in the sleeve when the rod is inserted partially into the sleeve, as shown in FIG. 3. In operation, pushing down on the rod with a relatively small force will allow the rod to frictionally grip the surrounding portion of the sleeve and transmit the force to the piston body. This operation can be similar to that of a conventional syringe, where applying force to the proximal end of the plunger causes the piston body to press onto any substance provided in the chamber, e.g., as shown in FIG. 2.

If the force applied to the rod exceeds a predetermined limit, the frictional interface may be configured to allow the rod to slip relative to the sleeve, such that the rod enters the sleeve further and no additional force is transmitted to the piston body. In this manner, the amount of force conveyed to the piston head—and thus the pressure applied to a material in the chamber to which the plunger is attached—is limited. This limiting force or pressure value can be determined based on characteristics of the frictional interface between the rod and the sleeve and the size of the piston body. In this manner, a simple force-limiting "clutch" mechanism can be provided in the plunger arrangement to prevent application of excessive force or pressure using the plunger. The desired maximum force or pressure is typically selected to avoid or lessen the likelihood of causing damage to adipose cells or other cells in the chamber when the plunger is pressed down, e.g., to force some impurities through a filter at the distal end of the chamber.

Example 4: An Apparatus for Contacting Biological Material (e.g., Adipose Cells or Tissue) with a Membrane Stabilizing Agent Damage to the harvested cells can be repaired or prevented by mixing the adipose tissue with a membrane stabilization agent (MSA) or cell protectant, such as, e.g., Poloxamer P188 or lipoic acid. The MSA or cell protectant can be provided in a solution that is either pre-loaded in the chamber or added to a solution container in communication with the chamber. Certain MSAs or cell protectants may also be provided, e.g., in the form of a solid such as a powder, or in liquid form. In the apparatus shown in FIG. 4, the top of the container is configured to be affixed to the distal end of the chamber, and a filter is optionally provided between the chamber and the solution container. The MSA or cell protectant is preferably sterile to avoid contamination of the cells or tissue being treated.

Figure 4:
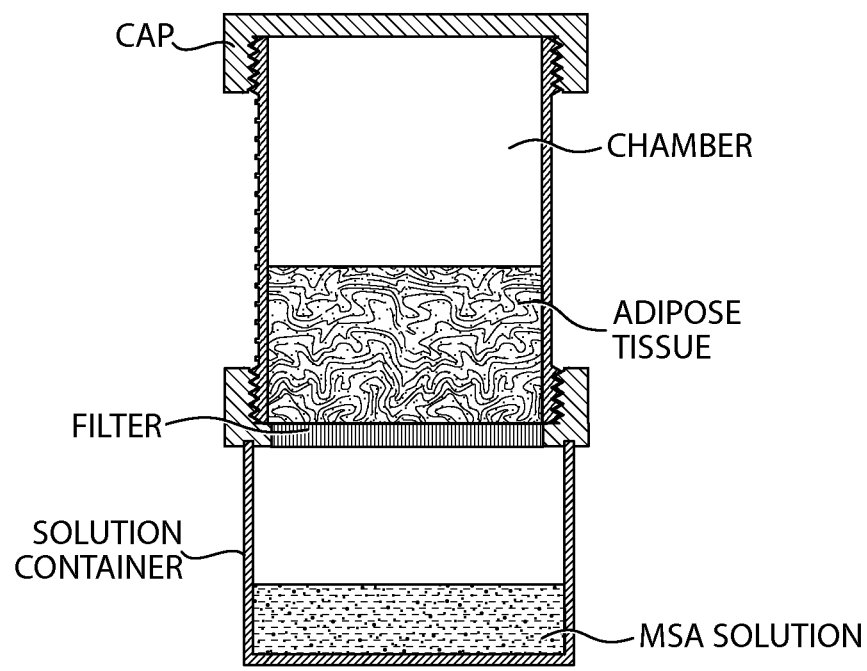
FIG. 4 depicts a non-limiting embodiment of an apparatus for contacting biological material (e.g., adipose cells or tissue) with a membrane stabilizing agent.

A cap is provided on the proximal end of the chamber as shown in FIG. 4. The MSA or cell protectant solution is introduced into the chamber and mixed with the adipose tissue therein by inverting the chamber/solution container assembly shown in FIG. 4, such that the MSA or cell protectant solution passes through the filter and into the chamber. Alternatively, a plunger mechanism may be affixed to the proximal end of the chamber, as shown in FIG. 2. The chamber/solution container assembly is inverted, and the plunger is partially withdrawn from the chamber to draw the MSA or cell protectant solution through the filter and into the chamber.

Figure 5:
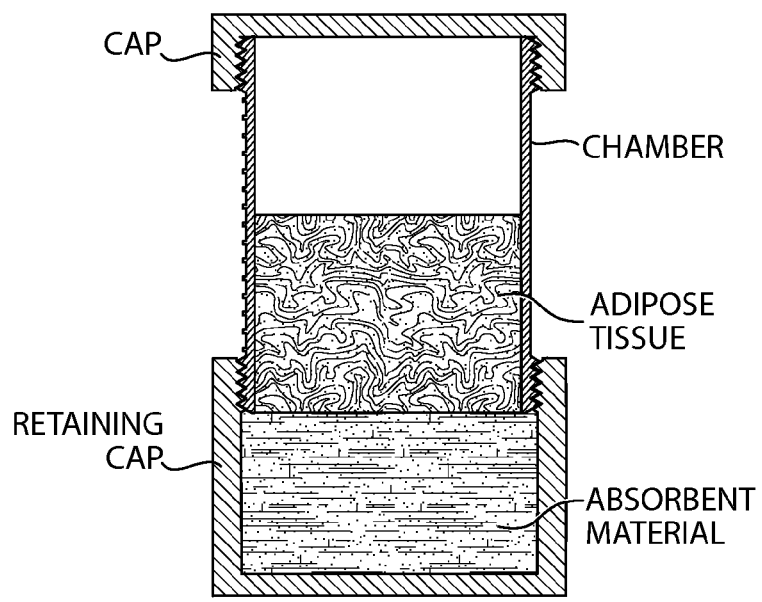
FIG. 5 depicts a non-limiting embodiment of an apparatus for contacting biological material with a retention matrix comprising an absorbent material.

Example 5: Apparatus for Contacting Biological Material with an Absorbent Material Impurities, including excess MSA or cell protectant if used, may be removed from adipose tissue in a chamber by providing an absorbent and/or adsorbent material in contact with the adipose tissue. For example, a water-absorbent material can be provided in a retaining cap that can be affixed to one end of the chamber as shown in FIG. 5. The chamber can then sit for a time interval or be gently shaken or agitated to provide sufficient contact between the adipose tissue and the absorbent material. After such contact has occurred for a sufficient time (e.g. 3 second to 5 minutes) the retaining cap with the absorbent material can be removed from the chamber, along with any absorbed water or other impurities that are present in the absorbing material. After this process, there will be fewer impurities remaining with the adipose cells in the chamber.

Figure 6:
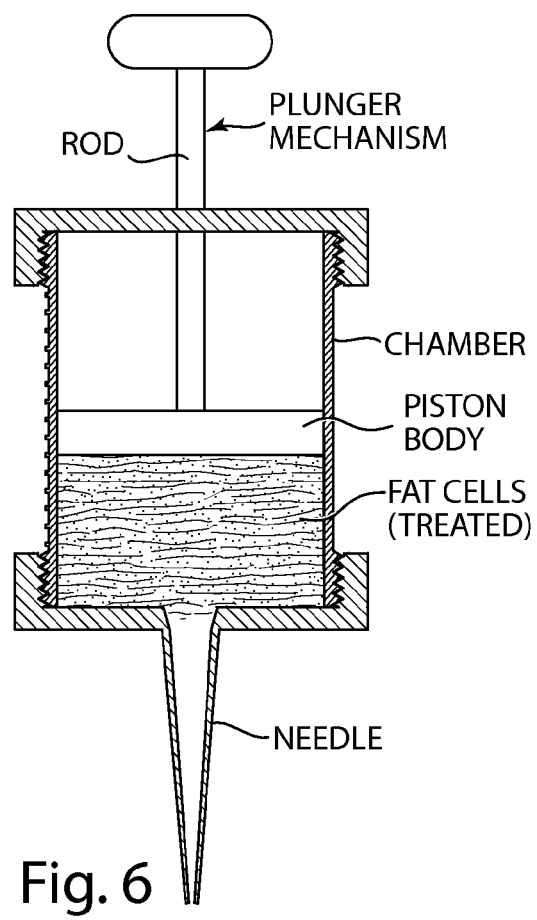
FIG. 6 depicts a non-limiting embodiment of an apparatus for transplanting biological material into a subject.

The cap shown in FIG. 5 may be of an elongated form to provide an absorbent enclosure similar to the waste cup shown in FIG. 2. At least a portion of the interior surface of the absorbent enclosure is provided with an absorbent material. The absorbent enclosure can be affixed to the distal end of the chamber to form a larger enclosure (e.g., similar to that shown in FIG. 2 with or without the central filter). Alternatively, a filter is used together with the absorbent enclosure. The filter element and absorbent enclosure are optionally provided as separate end-pieces that may be affixed to one another and to the chamber, or they are provided as a single end-piece that is affixed to the chamber. The adipose material with impurities (including any MSA or cell protectant, if used) is then be contacted with the absorbent material, e.g., by inverting the chamber/absorbent enclosure assembly. The relatively large area of the inner surface of the absorbent enclosure provides improved contact between the adipose tissue and the absorbent material to facilitate better absorption of impurities from the adipose tissue. This configuration also facilitates absorption of larger quantities of impurities (e.g., fluid, large volumes of an MSA or cell protectant solution) by the larger amount of absorbent material that can be provided in the absorbent container. The processed adipose tissue may be injected into a graft site in a subject using an apparatus as depicted in FIG. 6 or 10

Example 6: Dual Plunger Apparatus for Processing Biological Material

Figure 7:
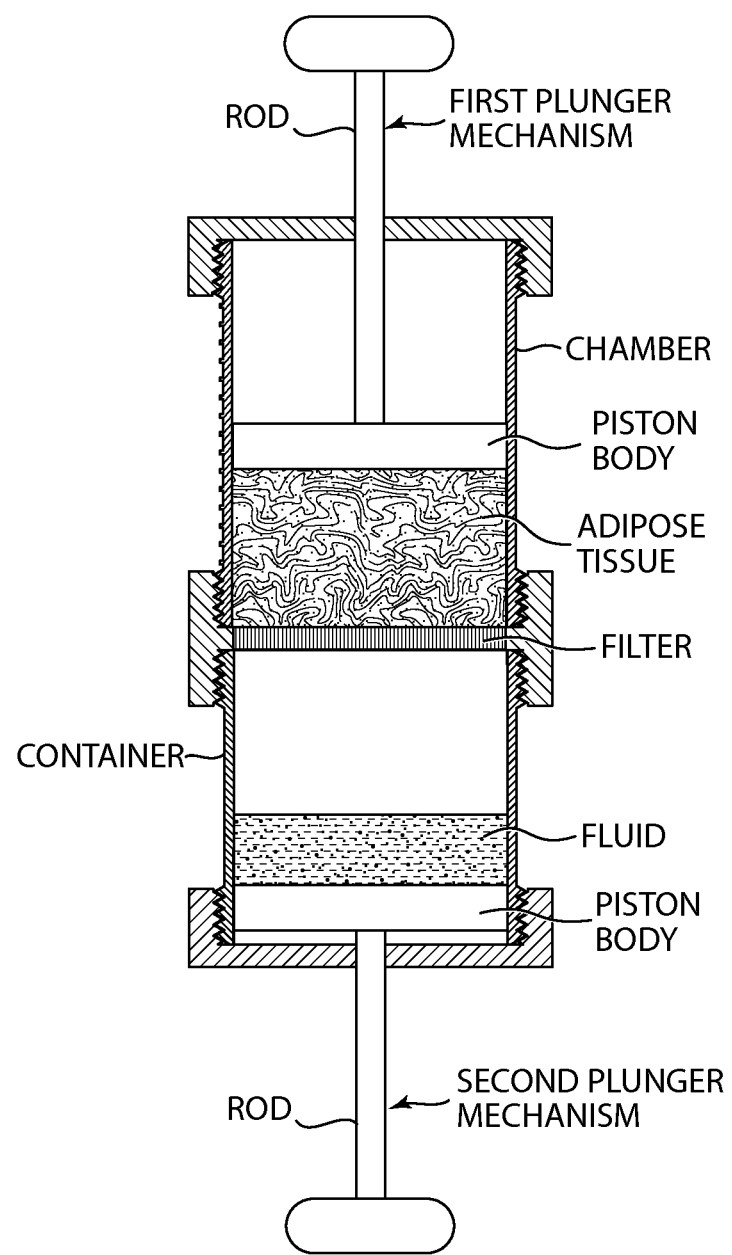
FIG. 7 depicts a non-limiting embodiment of an apparatus for processing biological material comprising a two-plunger arrangement to vary the effective volume in the chamber of the apparatus, to facilitate filtration, and/or to enable mixing of different agents with the biological material.

FIG. 7 depicts an apparatus comprising a dual-plunger arrangement to vary the effective volume in the chamber of the apparatus, to facilitate filtration, and/or to enable mixing of different agents with the biological material. An end-piece is provided that includes a container configured to be attachable to the chamber, and a further plunger or other similar arrangement at a distal end of the container (i.e., at the end of the container opposite the proximal end that is configured to be attached to the chamber or to another end-piece). The further plunger can be configured to vary the effective volume of the container when the plunger is translated. The further plunger can be formed as part of the container or it can be provided as a removable end-piece that can be affixed to an end of the chamber, similar to the upper end-piece/plunger arrangement shown in FIG. 7. The container may also include a filter or other restrictive but permeable barrier that is located between the container and the chamber, as shown in FIG. 7.

The apparatus shown in FIG. 7, can be used to facilitate introduction and/or removal of a liquid or fluid from the container to the chamber or vice-versa. For example, a first plunger located partially within the chamber is depressed while a second plunger partially within the container is simultaneously withdrawn. Such a "push-pull" operation can increase pressure in the chamber and reduce pressure within the container. This pressure differential is used to force a quantity of fluid to pass through the filter or other barrier and into the container. By reversing the direction of the plunger motions, fluid or liquid is forced into the chamber from the container. In certain embodiments, the motion of the two plungers is coupled, e.g., by connecting their respective rods with a mechanical coupling. In other embodiments, one plunger is depressed or withdrawn while the other plunger is allowed to move freely. This free motion accommodates the volume of material that passes from the container into the chamber or vice-versa when a force is applied to a single plunger.

The container may also contain a quantity of a MSA, cell protectant, or other fluid or liquid substance that is to be added to the biological material in the chamber. The container can be provided with a filter or other permeable barrier covering at least a portion of the end of the container that is configured to be affixed to the chamber. Properties of this filter can be selected to prevent leakage or spillage of the fluid in the container under atmospheric pressure, but allow the fluid to be introduced into the chamber when the container is affixed to an end of the chamber and a force is applied to one or both plungers.

A removable film or sheet can be provided over the filter end of the container for storage. Such film can further prevent leakage of a fluid from the container and/or help maintain sterility of the filter and contents of the container. Such a film can be peeled off or otherwise removed just prior to affixing of the container to the chamber. A film that which may be punctured to allow the MSA to flows into the biological material may also be provided.

The container shown in FIG. 7 may be empty initially, and used as a waste container for any fluids that are removed from the chamber through the filter, e.g., by applying a force to one or both plungers as described herein.

Example 7: Lipoaspirate Processing System

Figure 8A:
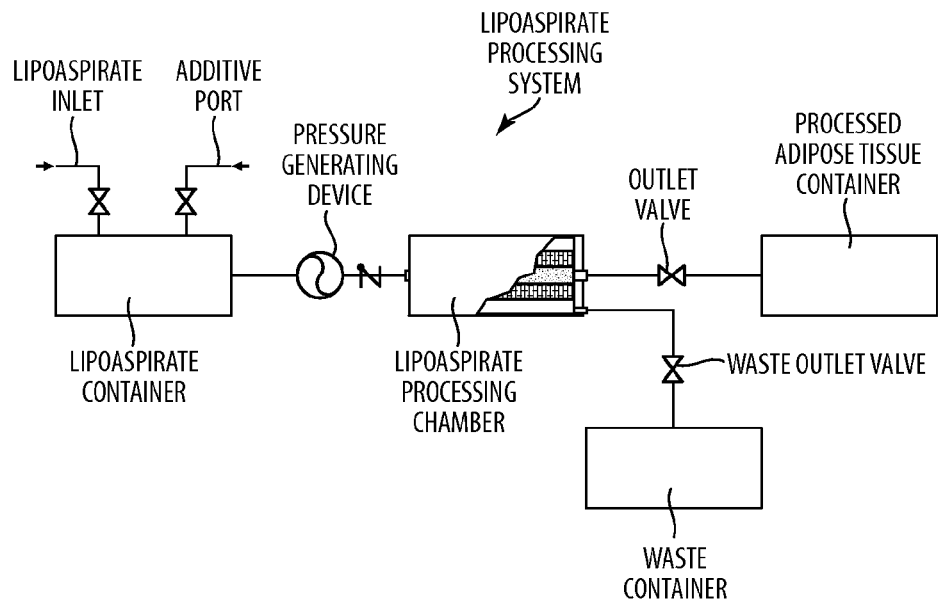
FIG. 8A depicts a non-limiting embodiment of a lipoaspirate processing system.

FIG. 8A depicts a lipoaspirate processing system. This system includes a lipoaspirate container for collecting lipoaspirate that has been obtained from a patient. Lipoaspirate enters into the lipoaspirate container through the lipoaspirate inlet. The lipoaspirate inlet is provided with an inlet valve for fluidically separating the inlet from the lipoaspirate container. The lipoaspirate container is also fluidically connected with an additive port that is provided with a valve for fluidically isolating the additive port from the lipoaspirate container. The additive port can be used for delivering a variety of different additives to the lipoaspirate that aid in processing of the lipoaspirate or that improve viability of the processed adipose tissue. Any of the components of this system may be coupled via separable or non-separable connections.

The lipoaspirate container is also fluidically connected to a lipoaspirate processing chamber. The processing chamber provides a container within which undesirable parts of the lipoaspirate are removed. Between the lipoaspirate container and the lipoapirate processing chamber is a pressure generating device. The pressure generating device draws lipoaspirate from the lipoaspirate container and drives the lipoaspirate into the lipoaspirate processing chamber through a check valve. The check valve in this configuration prevents backflow of processed lipoaspirate into the lipoaspirate container.

The lipoaspirate processing container may comprise a number of different components useful for isolating undesirable parts of the lipoaspirate. In some configurations the lipoaspirate processing chamber includes a filter for removing blood cells, cell debris, free lipids, extracellular material and other agents from the lipoaspirate. In some configurations, in order to drive filtrate through the filter, it is convenient to close the outlet valve and operate the pressure generating device to generate a positive pressure within the lipoaspirate processing chamber that is sufficient to move filtrate through the filter. The filtrate passes into waste cavity and exits the processing chamber through a waste outlet valve and into a waste container. The filtrate thus includes various undesirable parts of the lipoaspirate including cell debris, extracellular material and other agents.

The lipoaspirate processing chamber may also include other components including, for example, a retention matrix, immobilized antigen binding factors, or antioxidants for removing free radicals from the lipoaspirate.

The lipoaspirate processing system also includes a processed adipose tissue container, which is a container that is used for collecting adipose tissue that remains after processing the lipoaspirate. The processed adipose tissue is often suitable for injection directly into a subject for cosmetic or reconstructive purposes.

Figure 8B:
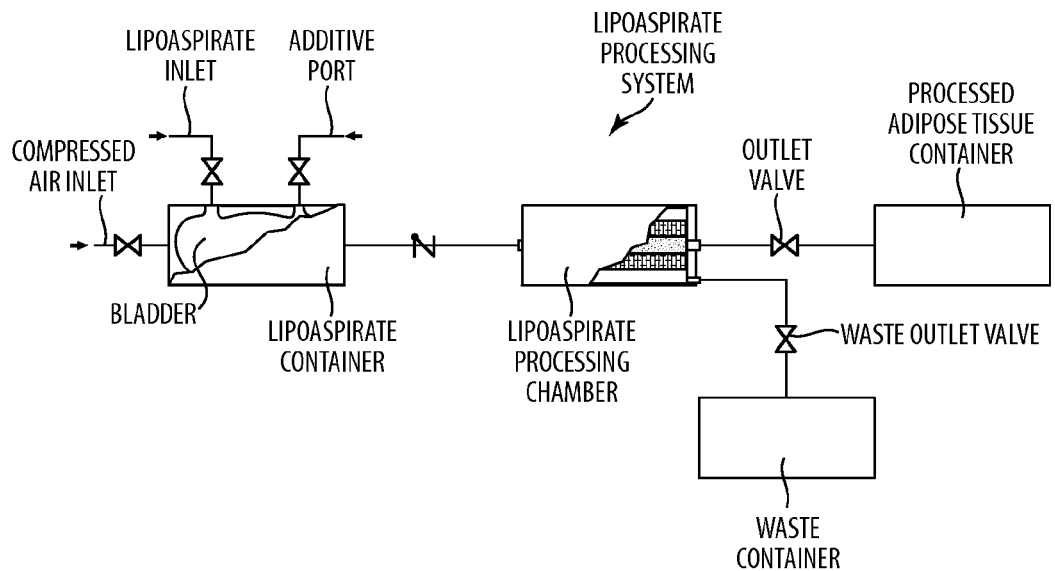
FIG. 8B depicts a non-limiting embodiment of a lipoaspirate processing system.

FIG. 8B depicts another configuration of a lipoaspirate processing system. This configuration is provided with a compressed air inlet that is fluidically connected with the lipoaspirate processing chamber. The lipoaspirate inlet and the additive inlet are fluidically connected with a bladder. Thus, lipoaspirate and any additives are collected within the bladder. The system is configured such that compressed air surrounds the bladder to drive fluid out of the lipoaspirate container towards the lipoaspirate processing container. In some configurations, the compressed air enters the lipoaspirate processing chamber with the lipoaspirate inlet valve and additive port inlet valve closed so that fluid does not pass back through the inlet lines. Alternatively, the inlet lines may be provided with inline check valves that prevent backflow of the lipoaspirate into the inlet lines.

Figure 8C:
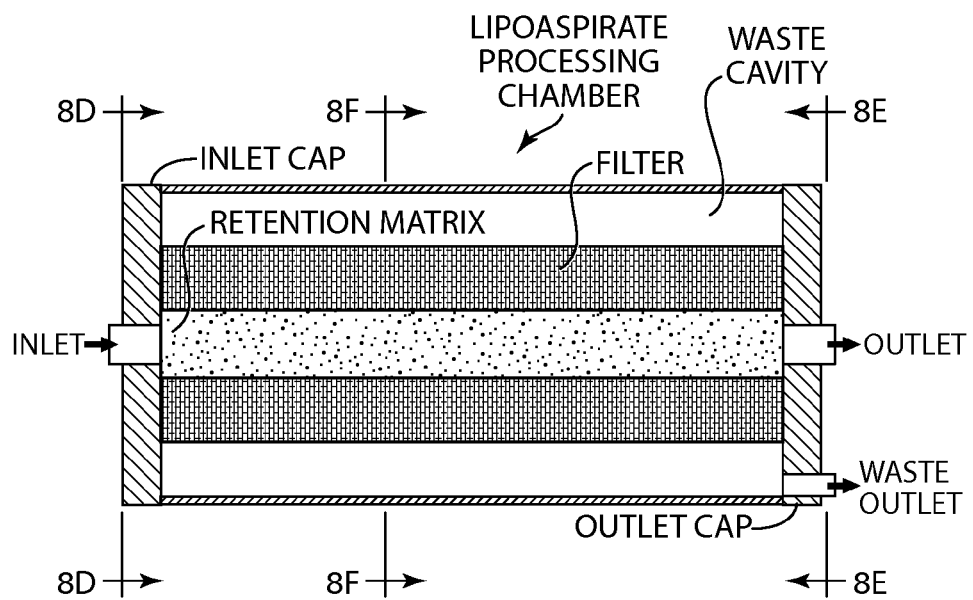
FIG. 8C depicts a non-limiting embodiment of a lipoaspirate processing chamber.

FIG. 8C depicts a cross-section of an exemplary lipoaspirate processing chamber. This lipoaspirate processing chamber comprises an inlet line that is fluidically connected with a retention matrix. The retention matrix may include, for example, a hydrophilic material and/or lipophilic material. The retention matrix is in contact with a surrounding filter. The filter is configured for allowing impurities to pass through the filter and into a waste cavity. As lipoaspirate moves through the chamber from the inlet toward the outlet, undesired parts of the lipoaspirate are retained in the matrix. In some cases, in order to facilitate filtration of the lipoaspirate, an outlet valve is closed such a sufficient positive pressure develops within the lipoaspirate processing chamber to allow for passage of filtrate through the filter and into the waste cavity. The filtrate in the waste cavity is removed from the lipoaspirate processing chamber by way of the waste outlet which is present in the outlet cap.

Figure 8D:
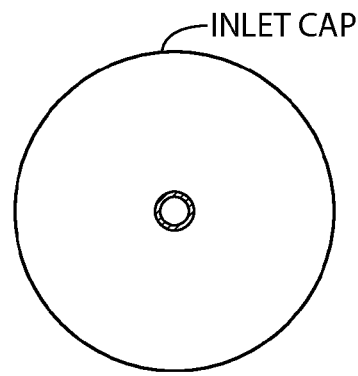
FIG. 8D depicts a non-limiting embodiment of an inlet cap of a lipoaspirate processing chamber.
Figure 8E:
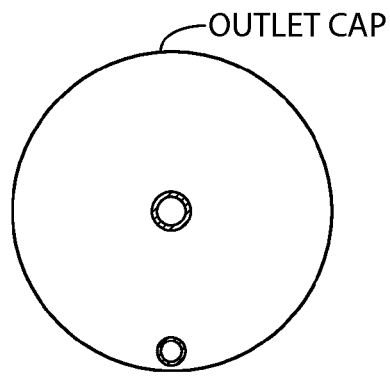
FIG. 8E depicts a non-limiting embodiment of an outlet cap of a lipoaspirate processing chamber.

FIGS. 8D and 8E depict alternative views of the inlet cap and outlet cap and depict the inlet and outlet ports of the lipoaspirate processing chamber.

Figure 8F:
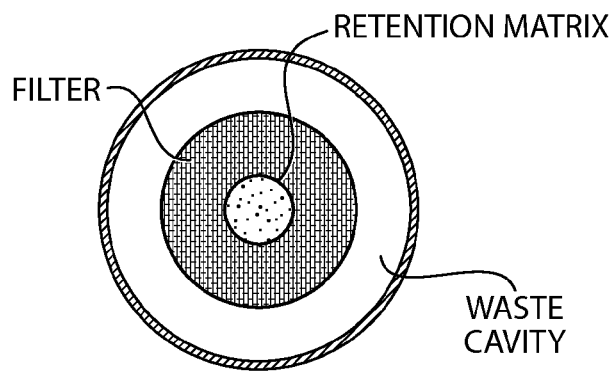
FIG. 8F depicts a non-limiting embodiment of cross-sectional view of a lipoaspirate processing chamber.

FIG. 8F depicts a cross-section of the lipoaspirate processing chamber and illustrates the presence of the retention matrix within and surrounded by the filter component which itself is surrounded by a waste cavity.

Example 8: Multi-Stage Lipoaspirate Processing System

Figure 9A:
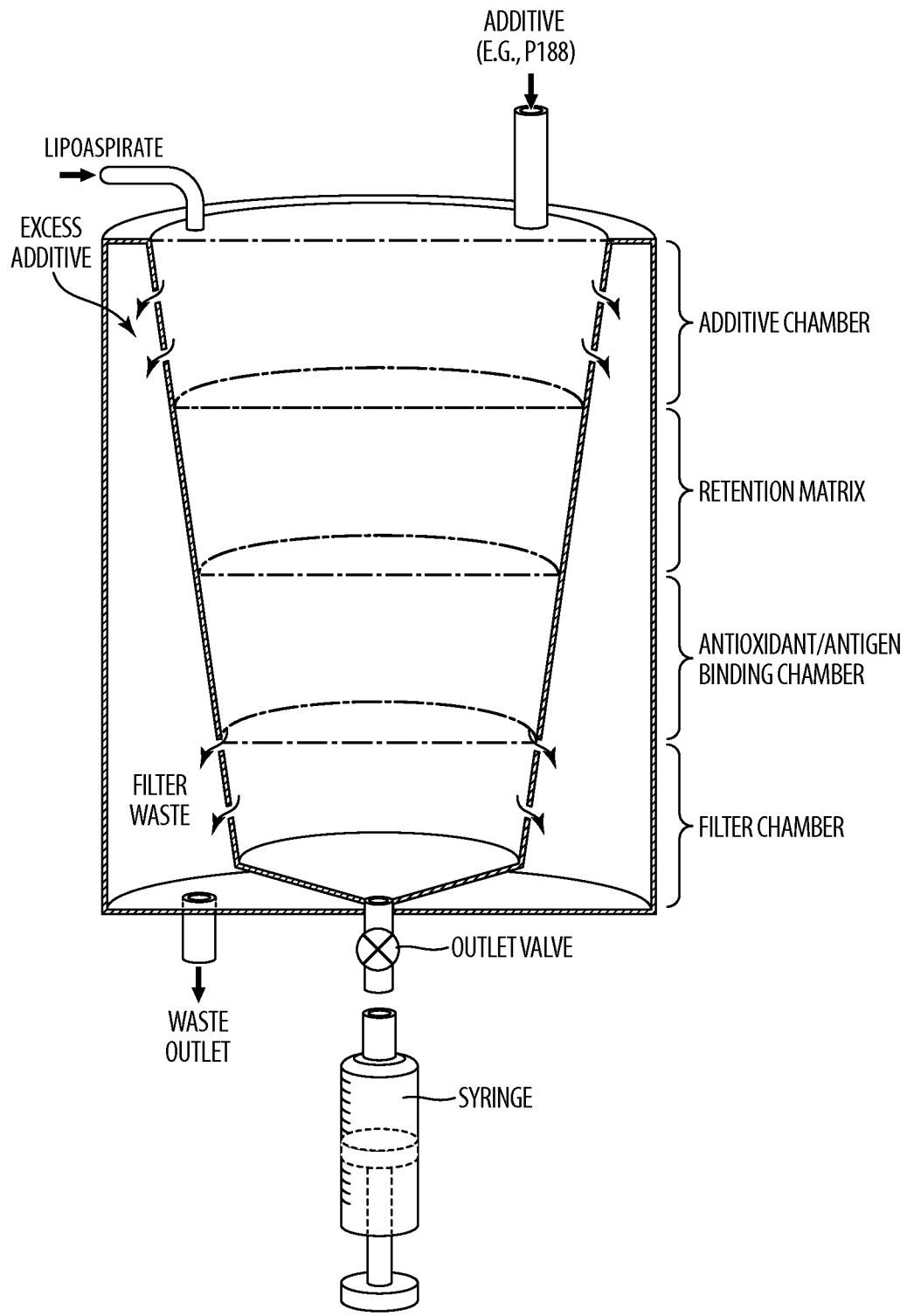
FIG. 9A depicts a non-limiting embodiment of a multi-stage lipoaspirate processing system.

FIG. 9A depicts a non-limiting embodiment of a multi-stage lipoaspirate processing system. This system includes an additive chamber, a retention matrix, an antioxidant/antigen binding chamber and a filter chamber. Lipoaspirate entering the system passes first into an additive chamber which is fluidically connected with an additive port for adding components such as membrane stabilizing agent, antioxidants and other components that may improve viability of the processed adipose tissue obtained from the lipoaspirate. The additives contact the lipoaspirate within the additive chamber and excess additive exits the additive chamber into a waste cavity. The second stage of the system comprises a retention matrix. The retention matrix may include, for example, one or more hydrophilic or lipophilic materials for retaining water and lipids (or other lipophilic molecules) from the lipoaspirate. The third stage of the system includes an antioxidant or antigen binding chamber. In this chamber, antioxidants and/or antigen binding factors are immobilized to a solid support, and in the case of antioxidants, sequester free radicals from the lipoaspirate, and in the case of the antigen binding agents, sequester one or more target antigens from the lipoaspirate. The fourth stage of the lipoaspirate processing system includes a filter configured for removing one or more undesirable parts of the lipoaspirate. The undesirable parts pass through the filter and exit as filtrate through filter waste ports into a waste cavity.

Excess additive and filtrate, present in the waste cavity, exit the system through a waste outlet port. Processed lipoaspirate, which comprises primarily adipose tissue suitable for injection into a subject, exits the lipoaspirate processing system through an outlet port which is configured with an outlet valve. Processed lipoaspirate may be directly added to a syringe (as depicted in FIG. 9A) that is suitable for injection directly into a subject. Alternatively, the processed lipoaspirate may be deposited into a container for later use or cryopreservation.

Figure 9B:
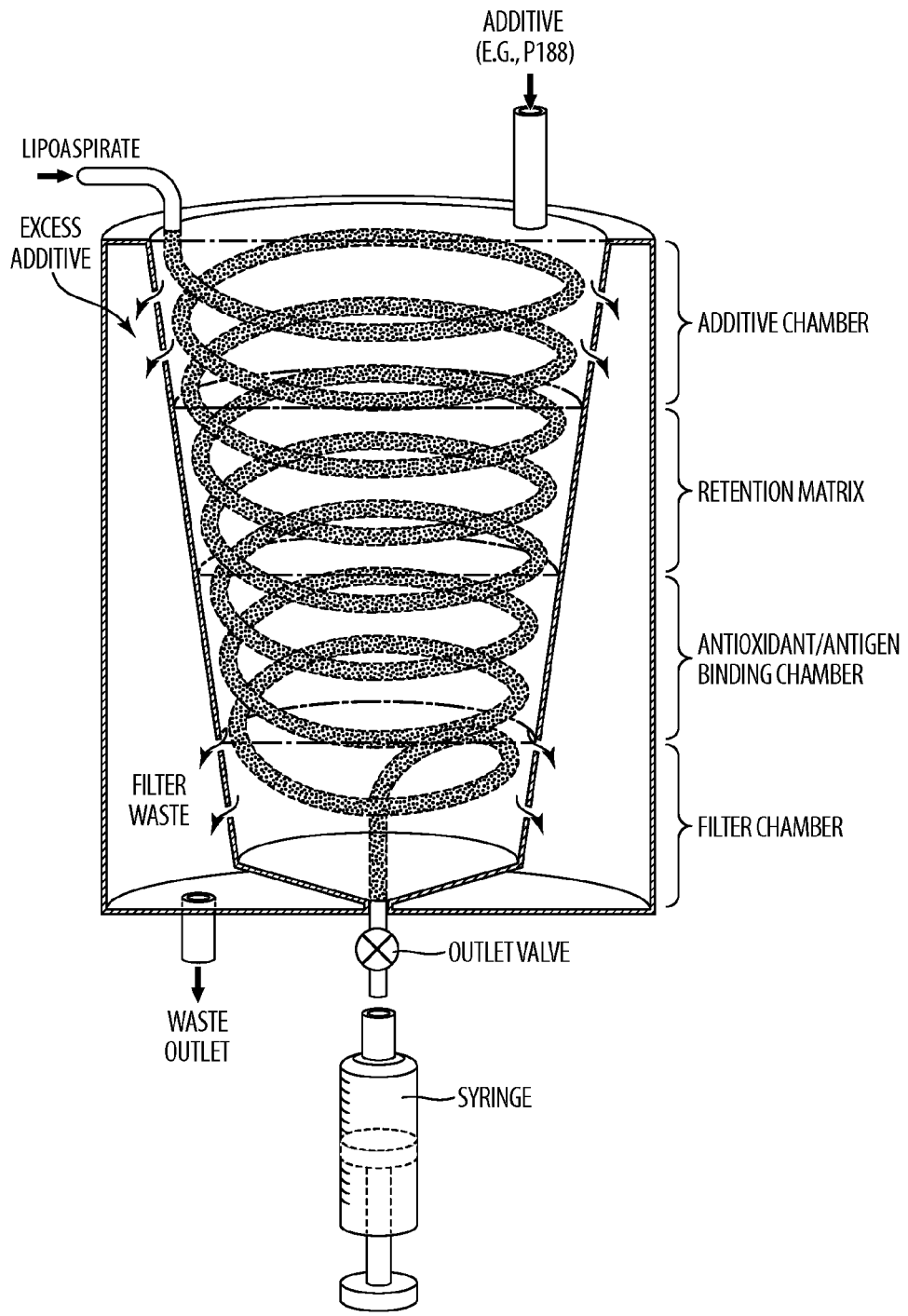
FIG. 9B depicts a non-limiting embodiment of a multi-stage lipoaspirate processing system.

FIG. 9B depicts an alternative configuration of a multi-stage lipoaspirate processing system. This configuration includes the coiled tube that passes through the various stages of the lipoaspirate processing system. The coiled porous tube(s) may pass through the entire system or may only be present in certain stages (e.g., additive stage and filter stage). The coiled tube is of a porous construction and allows additive in the additive chamber to freely contact the lipoaspirate. In the second stage, the lipoaspirate directly perfuses into the retention matrix, wherein certain undesirable parts (e.g., water, free lipids) of lipoaspirate are retained. Similarly, in the third stage, the lipoaspirate contacts immobilized antioxidants and/or immobilized antigen binding factors facilitating further removal of undesirable parts of the lipoaspirate. In the fourth stage, the lipoaspirate can freely contact the filter thereby allowing filtrate to pass through the filter into the waste cavity.

Figure 9C:
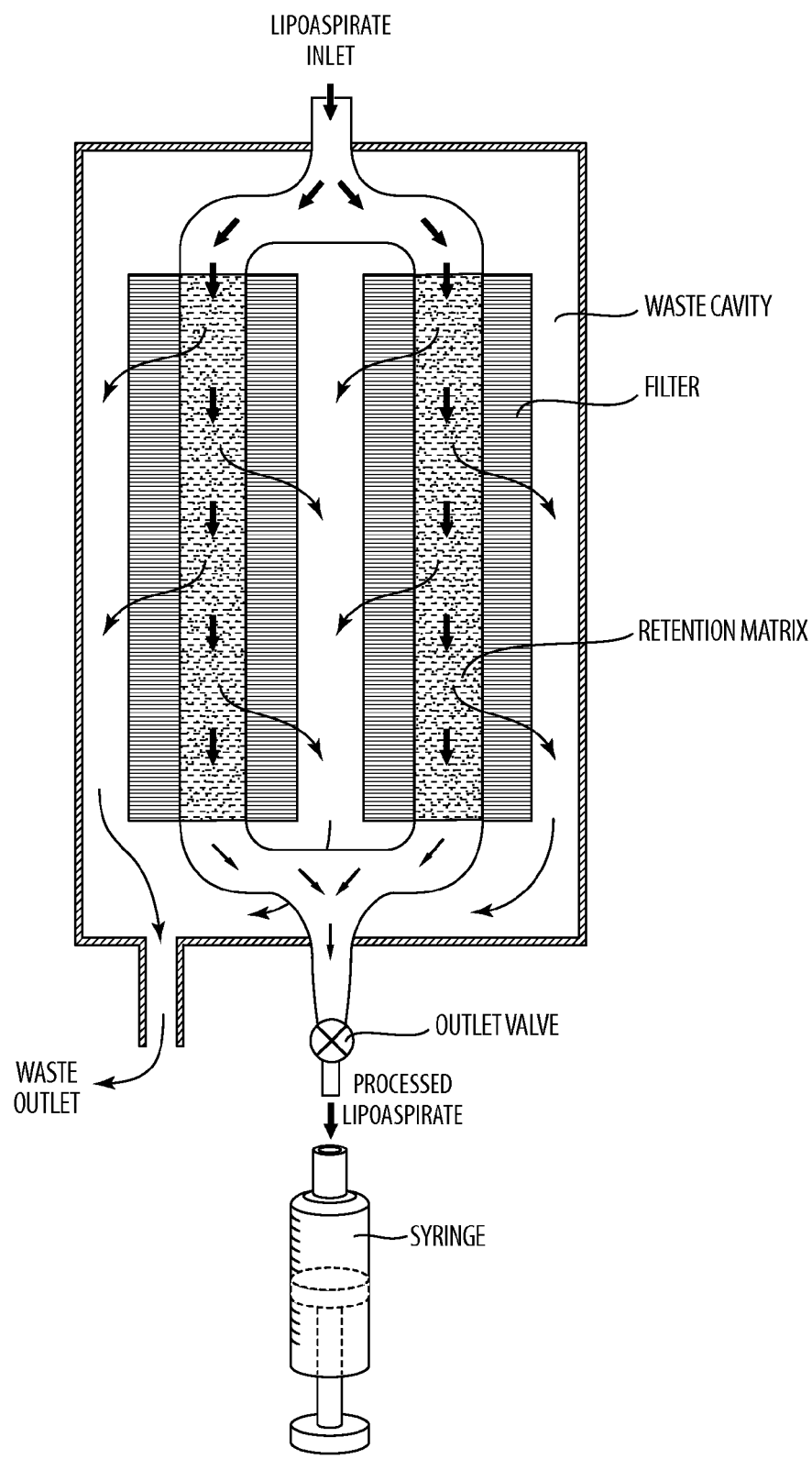
FIG. 9C depicts a non-limiting embodiment of a lipoaspirate processing chamber.

FIG. 9C depicts a lipoaspirate processing system in which lipoaspirate entering a processing chamber travels down multiple paths. Each path comprises a retention matrix surrounded by a filter. Lipoaspirate passing through either retention matrix will have undesirable parts retained within the retention matrix. A portion of the lipoaspirate will also pass through the filter. Typically, the outlet valve of the lipoaspirate processing chamber is closed to facilitate the generation of pressure within the lipoaspirate in order to drive filtrate through the filter. Filtrate passing through the filter enters into a waste cavity and passes out of the lipoaspirate processing chamber through a waste outlet valve. The processed lipoaspirate exits the lipoaspirate processing chamber through the outlet valve and may be added directly to a syringe for injection into a subject or may alternatively deposited into a container for later use or cryopreservation.

Figure 9D:
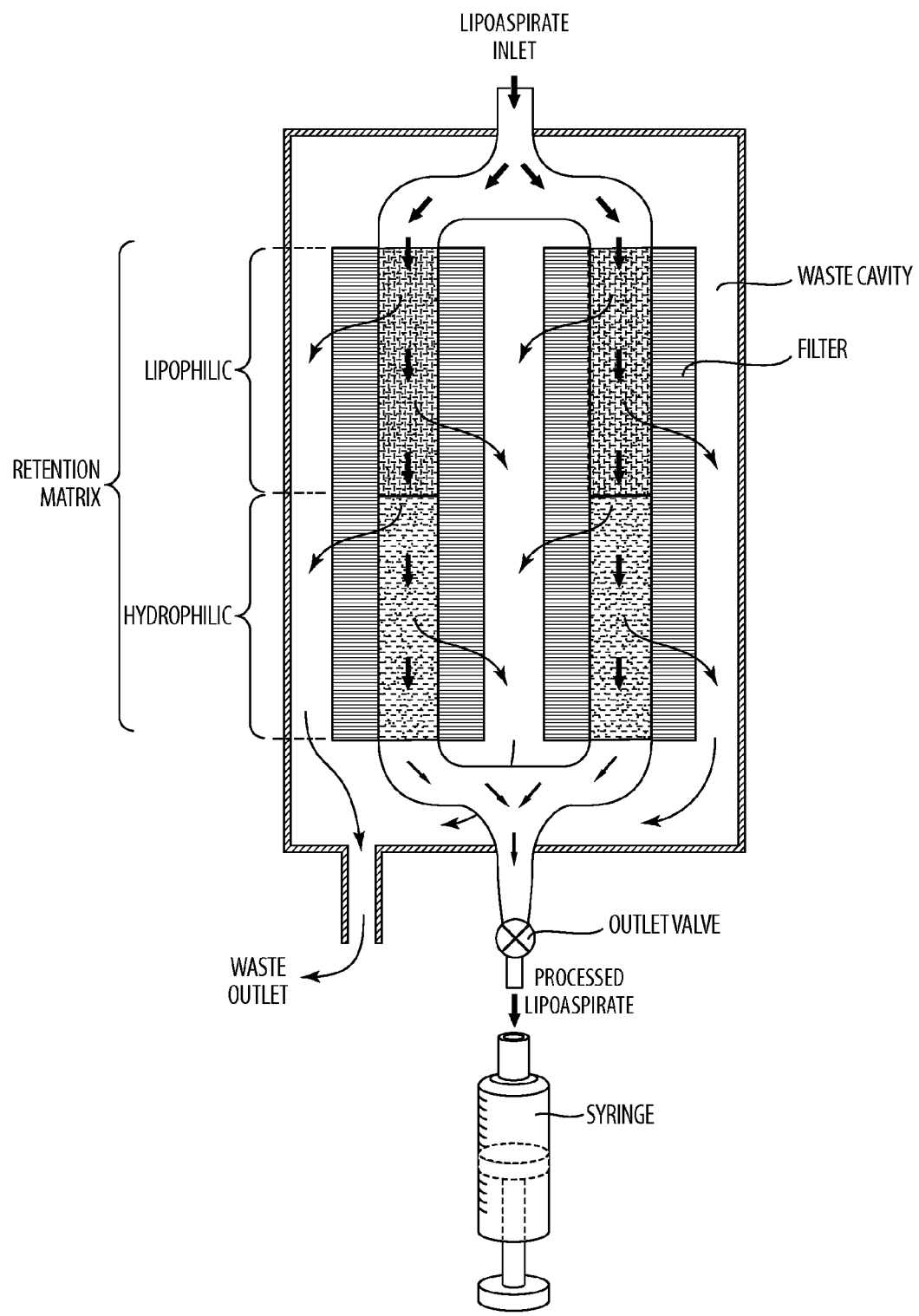
FIG. 9D depicts a non-limiting embodiment of a lipoaspirate processing chamber with retention matrix having a lipophilic region and a hydrophilic region.

FIG. 9D depicts another multipath lipoaspirate processing system. The chamber comprises a two-staged retention matrix that includes an upstream lipophilic portion and a downstream hydrophilic portion. In the lipophilic portion, lipids and other lipophilic molecules are retained in the retention matrix. In the hydrophilic portion, water and other hydrophilic molecules are retained. Filtrate passes through the filter, enters into the waste cavity and exits the system through the waste outlet. The processed lipoaspirate may be deposited into a syringe for injection directly into a subject or into a container for later use or cryopreservation.

Example 9: Apparatuses for Injecting Biological Material into a Subject

Figure 10A:
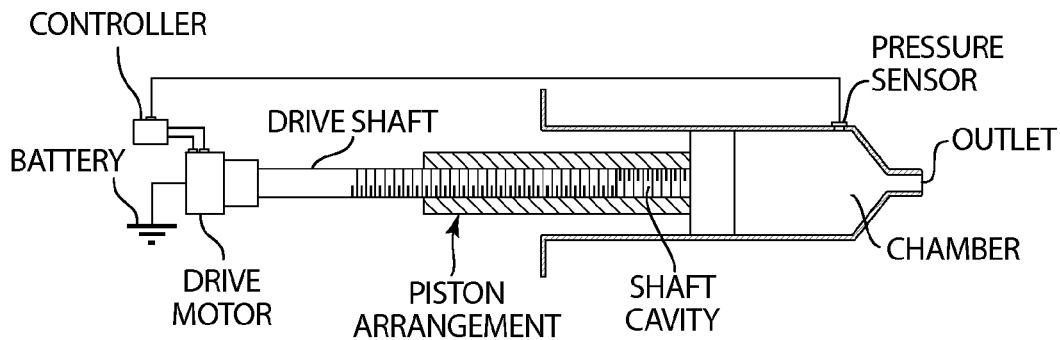
FIG. 10A depicts a non-limiting embodiment of an apparatus for injecting biological material into a subject.
Figure 10B:
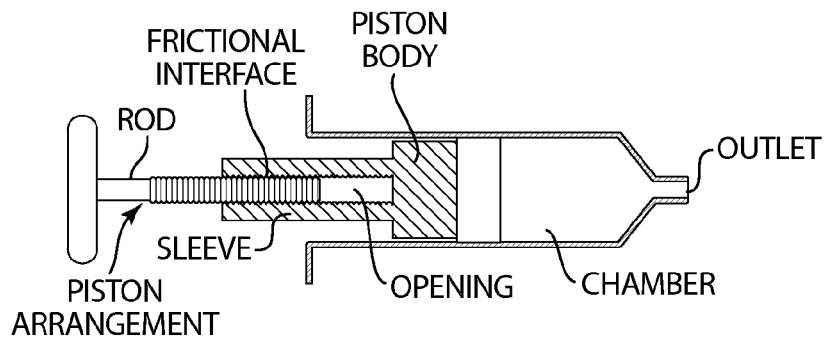
FIG. 10B depicts a non-limiting embodiment of an apparatus for injecting biological material into a subject.
Figure 10C:
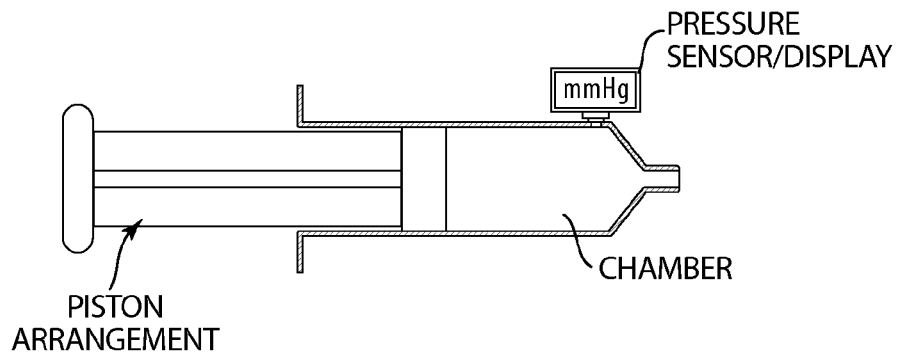
FIG. 10C depicts a non-limiting embodiment of an apparatus for injecting biological material into a subject.

FIGS. 10A-10C depict various apparatuses for injecting adipose tissue. The apparatus in FIG. 10A is configured with a chamber and a piston arrangement. The chamber is configured for housing adipose tissue to be injected into a subject. The apparatus includes a piston arrangement configured for generating a pressure within the chamber that drives the tissue out of the apparatus through the outlet. The piston arrangement in this configuration is coupled with a drive motor that functions as a piston displacement device. The drive motor turns a drive shaft which is coupled within a shaft cavity of the piston arrangement. Rotation of the drive shaft results in displacement of the piston arrangement toward the distal end of the apparatus thereby reducing the volume in the chamber. The drive motor can also be rotated in the opposite direction to drawn the piston arrangement toward the proximal end of the apparatus whereby the volume of the chamber increases.

The drive motor may be powered by a battery (as shown in FIG. 10A). However, alternative power sources may be used, including AC or AC-to-DC power supplies. Operation of the drive motor is controlled by a controller which is electrically connected to a pressure sensor. The pressure sensor senses pressure within the chamber, communicates an electrical signal indicative of the pressure within the chamber to the controller. The controller then operates the drive motor in response to the sensed pressure. This apparatus is configured to ensure that the drive motor operates at a rate such that the pressure within the chamber is within a predetermined maximum. By controlling pressure in the chamber in this way the velocity and shear stress imparted on the adipose tissue as it exits through the outlet can be controlled to ensure adequate viability of the adipose tissue.

The controller may also be configured to receive one or more user inputs. For example, a user may input a set-point pressure whereby the controller will operate the drive motor to maintain the user-specified set-point pressure.

FIG. 10B depicts an injection apparatus fitted with a mechanically controlled piston arrangement. This piston arrangement includes a frictional interface, in which a rod is connected to a sleeve through a frictional interface. The frictional interface is arranged and configured to limit the maximum force that may be generated by depressing the rod, and therefore, to limit the maximum pressure within the chamber. By controlling pressure in the chamber in this way the velocity and shear stress imparted on the adipose tissue as it exits through the outlet can be controlled to ensure adequate viability of the adipose tissue.

FIG. 10C depicts an injection apparatus fitted with a pressure sensor and display. The apparatus may be operated by depressing the piston arrangement by hand. The apparatus includes a pressure sensor with a display such that the user can monitor the pressure developed within the chamber and ensure that the pressure developed within the chamber does not exceed a pre-determined maximum. The pre-determined maximum being, as in the apparatus depicted in FIG. 10B, a pressure above which undesirable velocities and shear stresses will be imparted on the adipose tissue as it exits the outlet of the chamber.

Example 10: Autologous Fat Grafting

Summary

Fat grafting has recently become more prevalent due to low donor site morbidity, low complication rate, and fast recovery time. In this study, Applicants examined the role of aspiration and injection pressure on human fat grafts in a nude mouse model. Tumescent liposuction was performed in the laboratory on fresh panniculectomy specimens with a standard 4 mm cannula. Suction pressure was set to −15 inches Hg (−0.5 atmosphere) or −25 inches Hg (−0.83 atmosphere). Lipoaspirate was centrifuged at 1200G and the fat was injected into the flanks of nude mice with a 16 gauge angiocatheter. Fresh operating room lipoaspirate was centrifuged at 1200G and the fat was injected into nude mice using low or high injection pressures. After 4 weeks, the fat lobules were analyzed for weight and histology. With respect to aspiration pressure, high versus low suction pressures yielded no apparent differences in weight and histology. With respect to injection pressure, in a 3 cc syringe, injecting fat at a fast rate (3-5 ml/sec) versus slower rate (0.5-1 cc/sec) achieved pressures of 2744 mmHg (3.61 atm) versus 549 mmHg (0.722 atm), respectively ($p<0.001$). A low injection pressure yielded a 38% improvement in weight ($p<0.001$) over high injection pressure. This was also reflected in histology samples. In conclusion, changes in suction pressures did not affect fat grafts in vivo under the conditions examined. Lobules injected with high pressure, however, did not performed as well those injected with low pressure. These data indicate that it is injection pressure significantly affects fat graft survival.

Introduction to the Example:

Autologous fat grafting has become much more prevalent. It has a variety of cosmetic and reconstructive applications which range from breast augmentation to the treatment of facial hemiatrophy. Despite its utility, fat grafting is limited by unpredictable long-term results. This can necessitate multiple procedures and, as a result, increase the risk to the patient. One contributing factor for these inconsistent results is the wide variety of fat grafting techniques that are being utilized today. Improved techniques for autologous fat grafting are need. In this example, Applicant have examined the effects of aspiration and injection pressure on fat grafting.

Fat graft harvesting can be performed by either conventional machine liposuction or handheld syringe liposuction. Machine liposuction allows the user to control the suction pressure, which remains constant throughout the harvesting procedure. In handheld syringe liposuction, the suction pressure depends on the user. As the syringe fills with liposuction, the vacuum is reduced and the user must pull the plunger further back to achieve the same suction pressure. Applicant examined whether there is a difference in graft survival when harvesting with high or low suction pressure.

Injection pressure, can be affected by multiple variables. Applicant has recognized that injection flow rate is a parameter that may be controlled by the user. Poiseuille's law dictates that as the flow rate increases, there is a proportional increase in pressure. Applicant has examined the effect of increase flow rate (and pressure) on fat graft survival.

In this example, the role of aspiration and injection pressure in autologous fat grafting in a small animal model was examined.

Materials and Methods

Aspiration Pressure

Figure 11:
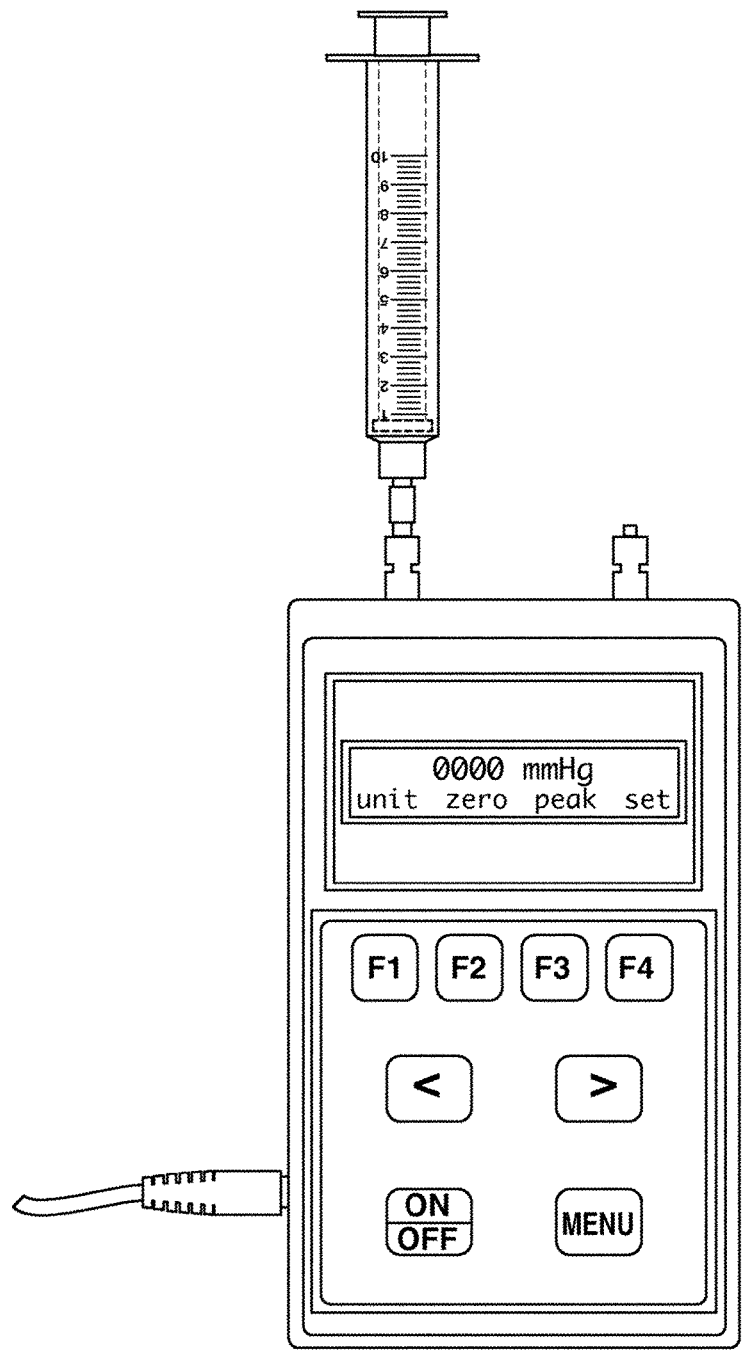
FIG. 11 depicts a non-limiting embodiment of a suction syringe manometer setup.

Suction pressure measurements using various syringes (3 ml, 10 ml, 60 ml syringe) were obtained using a manometer (Netech UniMano) (FIG. 11). Using a discarded tissue IRB protocol, fresh panniculectomy specimens were obtained from the operating room. Standard tumescent liposuction was performed using machine liposuction (Byron) and a standard 4 mm cannula (Mentor) using either −15 inch Hg (−0.5 atmospheres) or −25 inch Hg (−0.83 atmospheres) of suction pressure. Laboratory lipoaspirate was then centrifuged at 1200 G for 3 minutes in 50 ml conical centrifuge tubes. The fat layer was isolated and one milliliter aliquots were injected into the subcutaneous space of nude mice using a 16 gauge angiocatheter using a 3 ml syringe with a slow injection. After 4 weeks, animals were sacrificed and the fat lobules were harvested for analysis. All animal experimentation was performed under the protocols described by an approved animal protocol.

Injection Pressure

Figure 12:
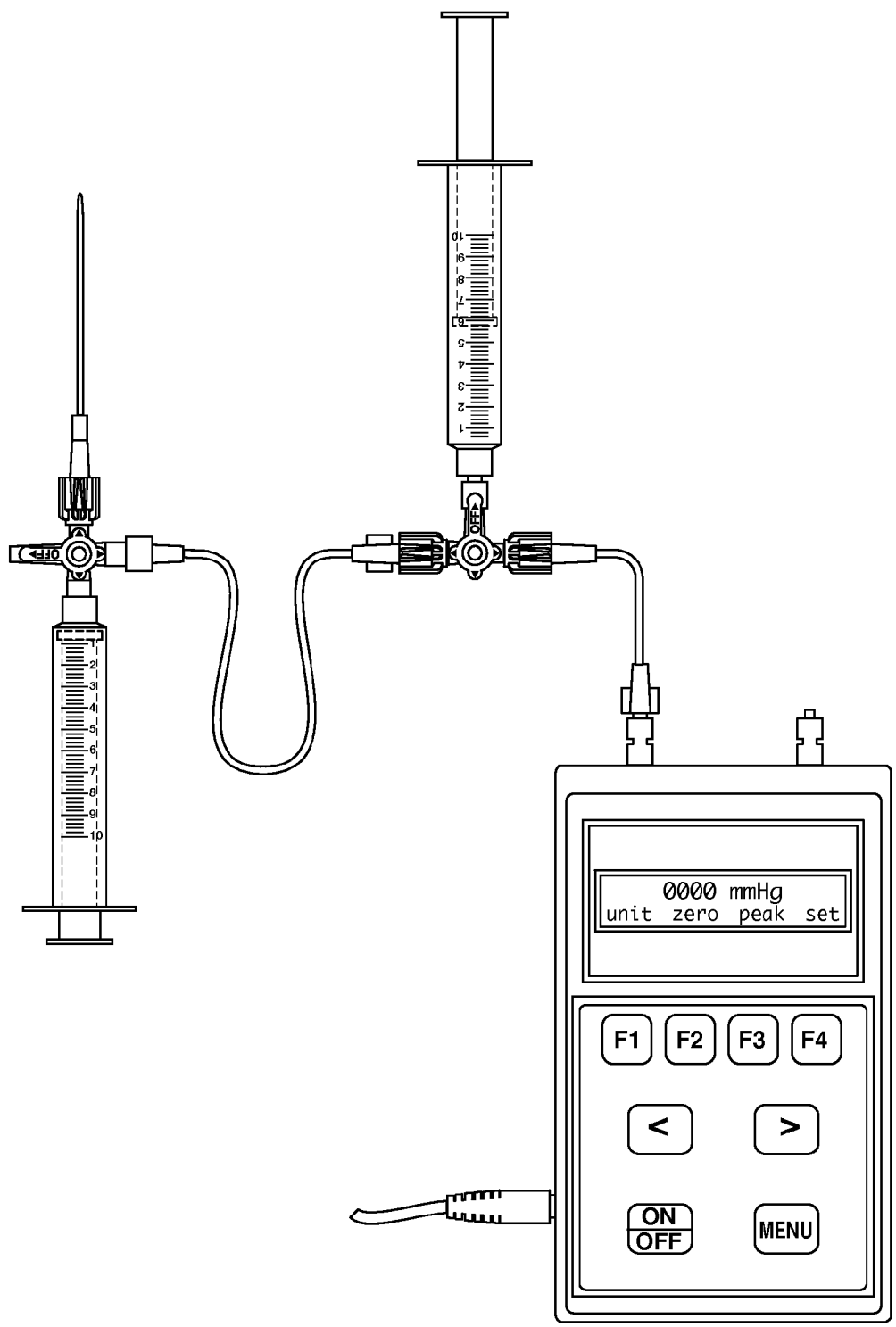
FIG. 12 depicts a non-limiting embodiment of an injection syringe with 16 gauge angiocatheter manometer setup.

Fresh liposuction was obtained from the operating room under a discarded tissue IRB protocol and centrifuged at 1200 G for 3 minutes in 50 ml conical centrifuge tubes. One ml aliquots using a 3 ml syringe were injected into the subcutaneous space of nude mice using a 16 gauge angiocatheter under an approved animal protocol. Animals were stratified to a slow injection group (0.5-1.0 ml/second) or a fast injection group (3-5 ml/second). Pressure measurements of fast and slow injections using the same angiocather and syringe size were then obtained using a manometer (FIG. 12). After 4 weeks, animals were sacrificed and the fat lobules were harvested.

Weight and Histology

Lobules were weighed using a benchtop scale (Ohaus) after explant. They were fixed in 10% formalin for 24 hours, processed for paraffin embedding, and stained with hematoxylin and eosin. Pictures were taken at 100× magnification using a light microscope (Nikon E600). Histology scores were generated by 3 independent and blinded investigators and averaged for each group. The scoring method is based on a previously published scale, which assesses healthy fat, vacuoles, infiltrate, and fibrosis. Each parameter was evaluated based on the following scale: 0=absence, 1=minimal presence, 2=minimal to moderate presence, 3=moderate presence, 4=moderate to extensive presence, and 5=extensive presence. The scores for vacuoles, infiltrate, and fibrosis were combined to form a score for total injury.

Statistical Analysis

Data are expressed as mean+/−standard error. One-factor analysis of variance was used to compare mean weights between experimental groups. Statistical significance was defined by a value of $p<0.05$.

Results

Aspiration Pressure

Figures 13, 14:
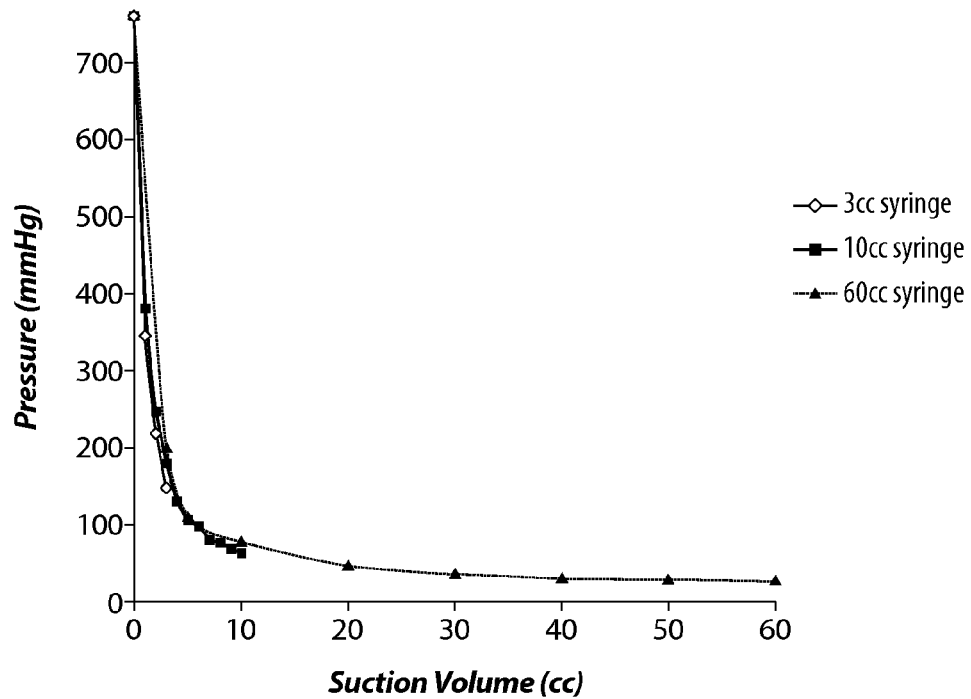
FIG. 13 depicts a suction syringe pressure chart.
FIG. 14 depicts suction syringe pressure curves.
Figure 15:
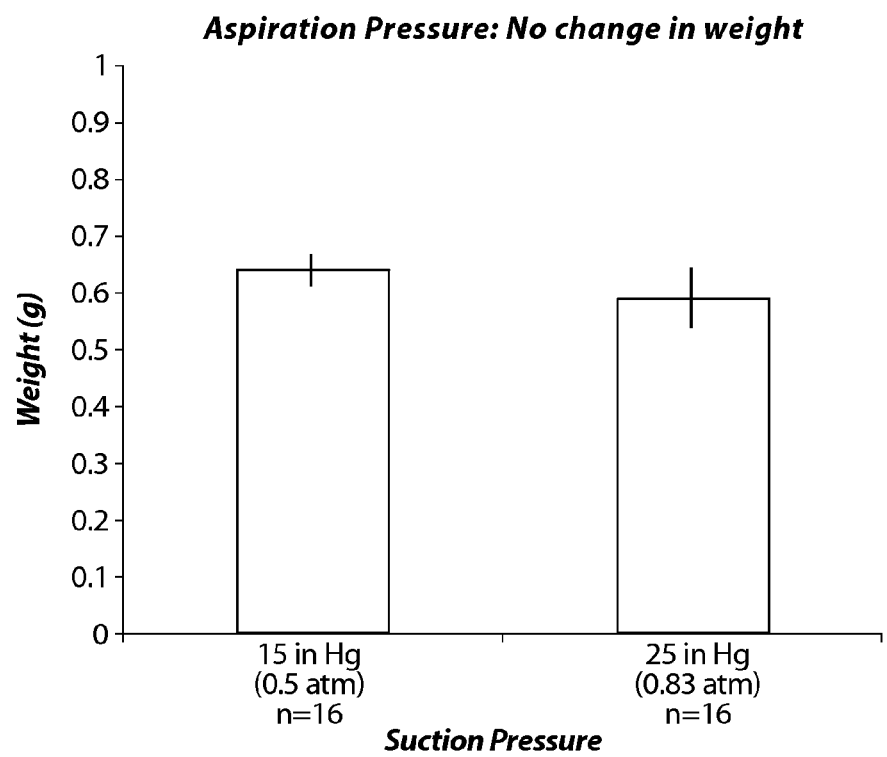
FIG. 15 demonstrates the effects of aspiration pressure on lobule weights.
Figure 16:
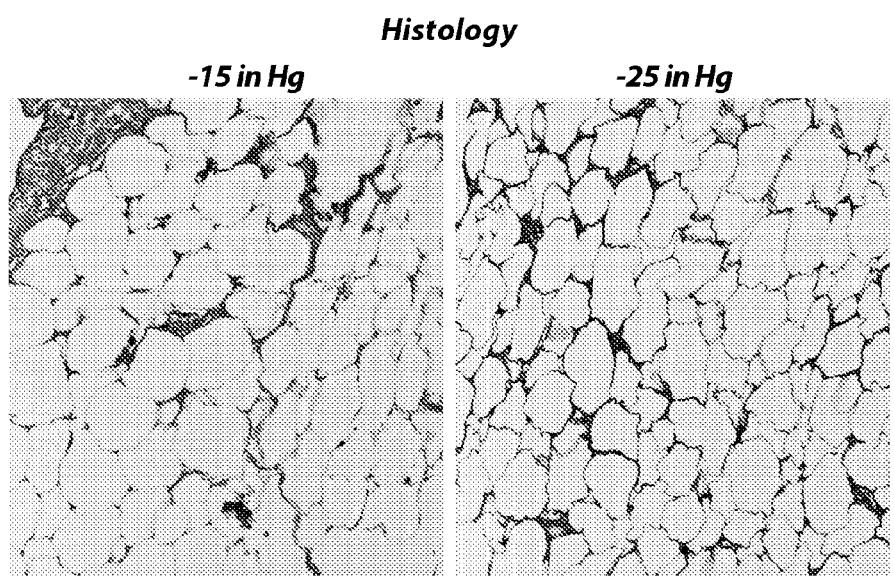
FIG. 16 demonstrates the effect of aspiration pressure on adipose tissue histology.

The maximum achievable suction (negative) pressures of 3 ml, 10 ml, and 60 ml syringes were −0.81, −0.92, and −0.96 atmospheres, respectively (FIGS. 13 and 14). In vivo, the average weight of lobules suctioned with −15 inch Hg (0.5 atm) versus −25 inch Hg (0.83 atm) were 0.64+/−0.03 grams (n=16) and 0.59+/−0.06 grams (n=16), respectively (p=0.462). These were not statistically significant (FIG. 15). Histologic examination demonstrated similar degrees of healthy adipocytes, vacuoles, infiltrate and fibrosis (FIG. 16). Furthermore, scoring these parameters yielded a minimal difference (FIG. 17) between −15 inch Hg group (n=4) and −25 inch Hg group (n=3).

Injection Pressure

Figure 18:
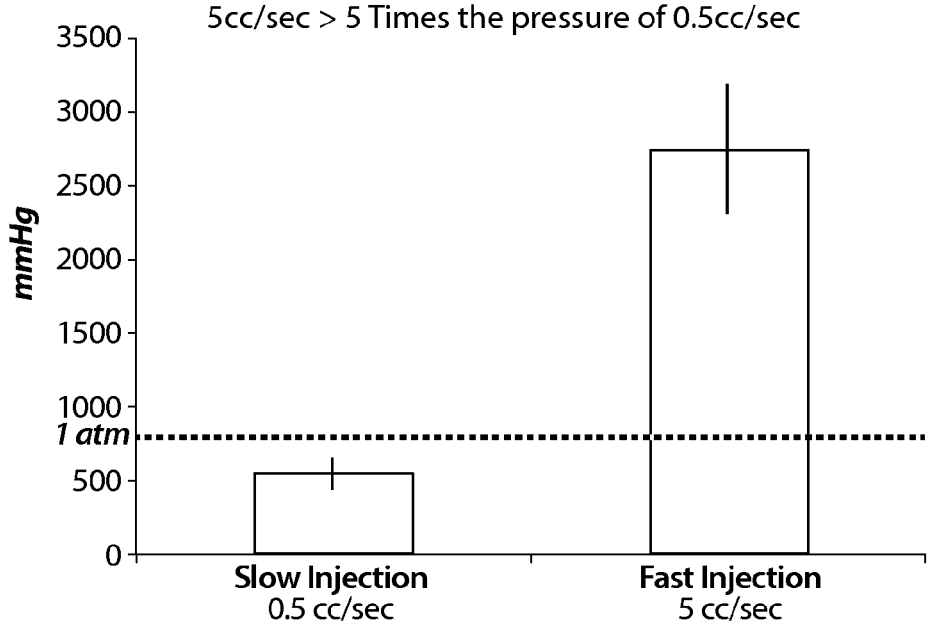
FIG. 18 demonstrates the effect of injection pressure readings from adipose tissue injected through a catheter or syringe.
Figure 19:
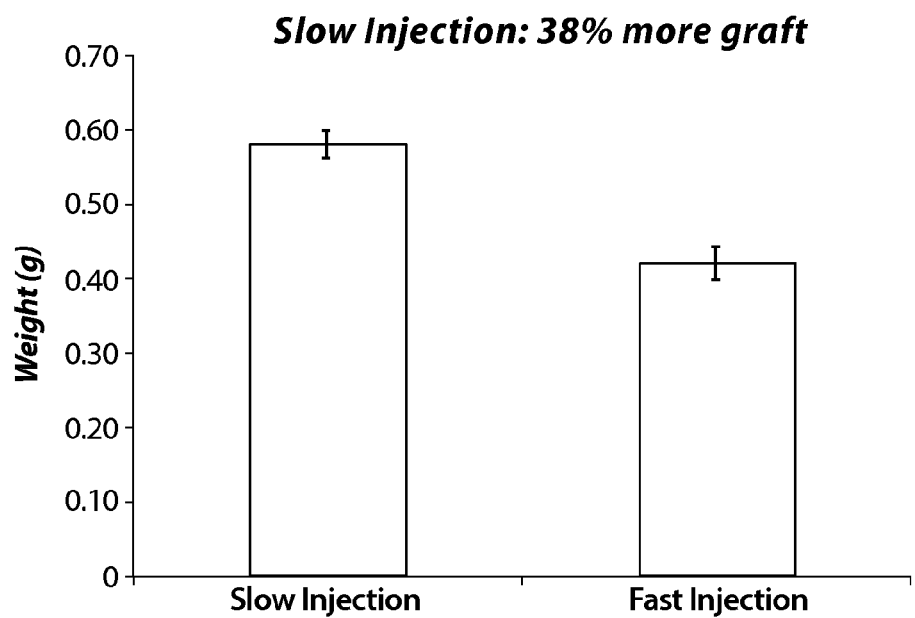
FIG. 19 demonstrates the effect of injection pressure on lobule weights.
Figure 20:
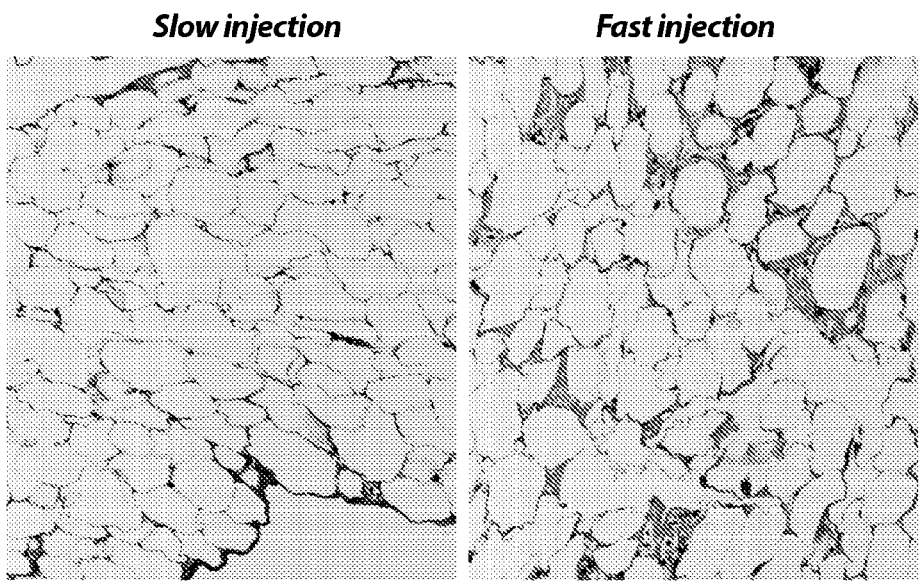
FIG. 20 demonstrates the effect of injection pressure on adipose tissue histology.
Figure 21:
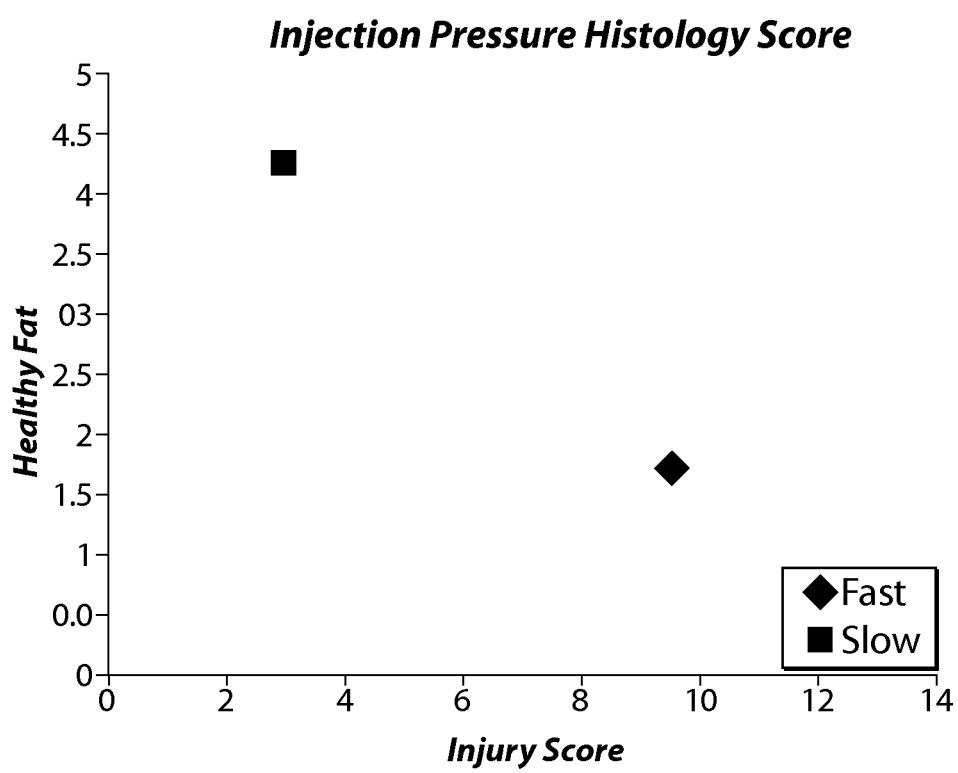
FIG. 21 demonstrates the effect of injection pressure on adipose tissue histology scores.

Pressure readings of fat injected through a 16 gauge angiocatheter at slow (0.5-1.0 ml/sec) versus fast (3-5 ml/sec) rates were 0.72 and 3.61 atmosphere, respectively (FIG. 18). In vivo, lobules injected with slow versus fast flow rates yielded an average weight of 0.58+/−0.02 grams (n=32) versus 0.42+/−0.02 grams (n=30), respectively (p<0.001). This represented a 38% improvement in weight in lobules injected slowly (FIG. 19). Histologic appearance also demonstrated more healthy adipocytes with less vacuoles, infiltrate, and fibrosis (FIG. 20). This was also reflected in scoring assessment which demonstrated a significant increase in healthy adipocyte scores as well as a significant decrease in injury scores (FIG. 21) in lobules injected slowly (n=17) versus those with fast injections (n=13).

Discussion

Negative (aspiration) pressure and positive (injection) pressure are two distinct entities. The extremes of achievable pressures range from zero (i.e. perfect vacuum or outer space) to infinity (theoretical). At or near sea level, the atmospheric pressure is equal to 1 atmosphere. The negative (or positive) pressure obtained in a syringe is the difference between inside and outside the syringe. Therefore if the pressure inside of a syringe is reduced to 0.75 atmospheres and the pressure outside is 1 atmosphere (sea level), then the negative pressure achieved is −0.25 atmospheres. Since the absolute minimum pressure achievable is zero, then the maximum negative pressure achievable at sea level is −1 atmosphere. This does not apply to positive pressure because there is no theoretical maximum pressure. Therefore, changes in pressure can be much greater when injecting fat.

A second applicable principle is that handheld syringe liposuction depends mainly on Boyle's law which states:

$$Pressure_1 \times Volume_1 = Pressure_2 \times Volume_2$$

Therefore the pressure change is dependent on the ratio between the initial volume and the final volume. If the syringe plunger starts at the zero mark, then the initial volume is equal to the volume inside the suction cannula (often less than one ml). This concept is important when measuring suction pressures with a manometer because the starting volume must be similar. Introducing any tubing between the manometer and the syringe increases the starting volume enough to produce inaccurate results. The measured pressures achieved with various syringes (FIGS. 13 and 14) followed this principle and changed essentially only with respect to the volume change. The differences in achievable pressures were minimal and all approached but did not surpass −1 atmosphere.

Traditional handheld syringe liposuction is performed by withdrawing approximately 1 to 2 ml in a 10 ml syringe. The data provided herein show that this is roughly equivalent to −15 to −20 inch Hg set on a liposuction machine (FIG. 13).

Figure 17:
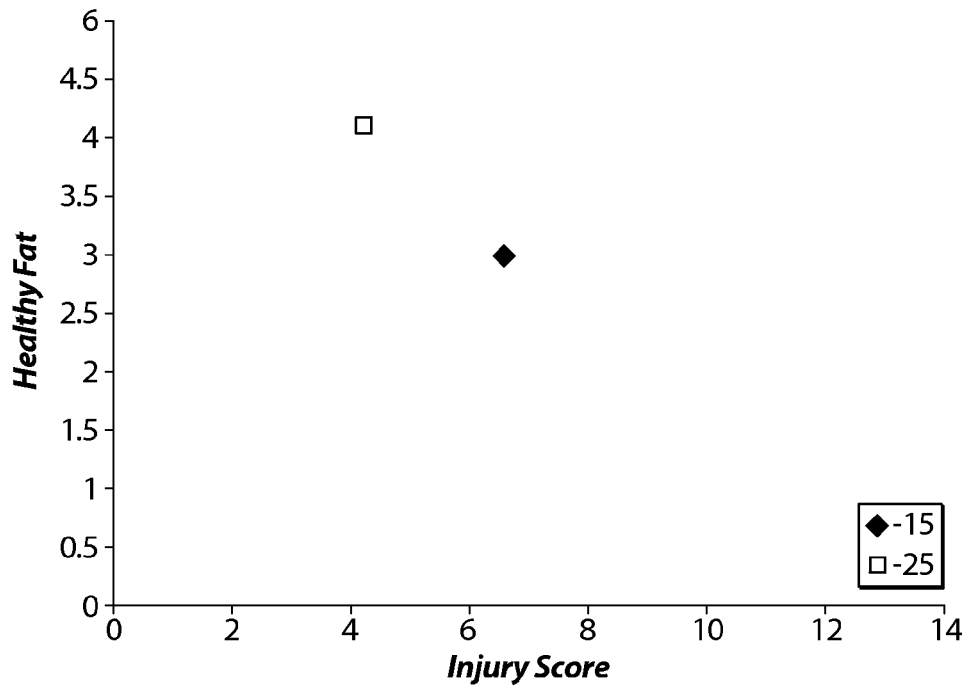
FIG. 17 demonstrates the effect of aspiration pressure on adipose tissue histology scores.

In the animal model, harvesting fat at −15 inch Hg, a typical handheld syringe liposuction pressure, and −25 inch Hg, a typical machine liposuction pressure, did not demonstrate a difference either by weight or by histology (FIGS. 15, 16, and 17). This is clinically relevant at least because machine liposuction on high pressure can be used without fear of affecting fat graft viability. This can oftentimes be an easier and more efficient method of fat graft harvesting.

As previously mentioned, injection pressure can be affected by many variables including flow rate. Injecting fat through a 16 gauge angiocatheter at a fast flow rate (3-5 ml/sec) produced a pressure five times that of a slow injection (0.5-1.0 ml/sec). In our animal model, fat grafts injected slowly yielded a 38% improvement by weight when compared to those injected with a fast flow rate. These fat grafts also appeared healthier on histology with less vacuoles, fibrosis, and infiltrate. Table 1 outlines injection velocities at different flow rates and catheter sizes.

TABLE 1

Injection Velocities through Various Catheters

| Catheter | Nominal Inner Diameter | | | Volumetric Flow Rate (ml/sec) | | | | | | | |
|---|---|---|---|---|---|---|---|---|---|---|---|
| Gauge | inches | mm | | 0.125 | 0.25 | 0.5 | 1 | 2 | 3 | 4 | 5 |
| 12 | 0.085 | 2.159 | Velocity | 3.4 | 6.8 | 13.7 | 27.3 | 54.6 | 81.9 | 109.3 | 136.6 |
| 13 | 0.071 | 1.803 | (cm/sec) | 4.9 | 9.8 | 19.6 | 39.2 | 78.3 | 117.5 | 156.7 | 195.8 |
| 14 | 0.063 | 1.6 | | 6.2 | 12.4 | 24.9 | 49.7 | 99.5 | 149.2 | 198.9 | 248.7 |
| 15 | 0.054 | 1.372 | | 8.5 | 16.9 | 33.8 | 67.6 | 135.3 | 202.9 | 270.6 | 338.2 |
| 16 | 0.047 | 1.194 | | 11.2 | 22.3 | 44.7 | 89.3 | 178.6 | 267.9 | 357.2 | 446.6 |
| 17 | 0.042 | 1.067 | | 14.0 | 28.0 | 55.9 | 111.8 | 223.7 | 335.5 | 447.3 | 559.2 |
| 18 | 0.033 | 0.838 | | 22.7 | 45.3 | 90.7 | 181.3 | 362.6 | 543.9 | 725.2 | 906.6 |

Without wishing to be limited to theory, a possible factor contributing to the observation that injection pressure affects fat graft survival while aspiration pressure does not, is that pressure has a direct traumatic effect on adipocytes which will ultimately cause cell death and graft resorption. This could be explained by the fact that the maximum negative pressure achieved is −1 atmosphere, while the maximum achievable injection pressure is far greater. In our experiments, the average pressure of a fast injection was 3.61 atmospheres. Therefore, it is possible to apply much greater pressure on fat grafts during injection than during suction/aspiration. By minimizing injection pressure, and resulting velocity and shear stress, trauma to fat grafts can be minimized thereby improving fat graft survival.

CONCLUSIONS

Changes in suction/aspiration pressures did not affect fat grafts in vivo under the conditions examined. Lobules injected with low pressure, however, yielded a 38% improvement by weight and had improved appearance on histology. These data indicate that it is injection pressure significantly affects fat graft survival.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Certain embodiments of the present invention provided herein are described primarily in terms of treatment and purification of adipose tissue to obtain samples of viable adipose cells for transplantation. However, these embodiments may be used to treat or process other biological materials, such as other tissues or cells (e.g., stem cells).

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An apparatus comprising
a chamber having an inlet and a first outlet;
a retention matrix within the chamber configured and arranged for contacting a biological material, when present in the chamber, such that a fraction of the biological material is retained in the retention matrix, wherein the retention matrix comprises at least one selected from the group of a lipophilic matrix that retains lipids from the biological material and a hydrophilic matrix that retains water from the biological material; and
a filter within the chamber that is configured and arranged for contacting the biological material, when present in the chamber, such that a waste fraction of the biological material passes through the filter;
wherein the inlet is fluidly connected to the first outlet along a first flow path that does not pass through the filter.

2. The apparatus of claim 1, wherein the first outlet is fluidically connected to an appropriately sized cannula or catheter.

3. The apparatus of claim 2, wherein the appropriately sized cannula or catheter is 12 gauge, 14 gauge, 15 gauge, 16 gauge, 17 gauge, or 18 gauge.

4. The apparatus of claim 1, wherein the chamber is configured and arranged to contain 1 ml to 1 L of the biological material.

5. The apparatus of claim 1, wherein the biological material is present in the chamber.

6. The apparatus of claim 1, further comprising the biological material, wherein the biological material comprises adipose tissue or a component thereof.

7. The apparatus of claim 6, wherein the adipose tissue or a component thereof comprises adipocytes, adipogenic cells, mesenchymal cells or stem cells.

8. The apparatus of claim 1, further comprising a membrane stabilization agent (MSA) in the chamber.

9. The apparatus of claim 8, wherein the MSA is a tri-block co-polymer comprising a tri-block co-polymer of the form: polyethylene glycol-polypropylene glycol-polyethylene glycol.

10. The apparatus of claim 9, wherein the MSA is poloxamer P188.

11. The apparatus of claim 8, wherein the retention matrix retains at least one selected from the group of water, lipids, metals, the membrane stabilization agent, and blood cells within the retention matrix.

12. The apparatus of claim 1, further comprising a pressure generating device that controls a pressure within the chamber.

13. The apparatus of claim 12, wherein the pressure generating device is a pump.

14. The apparatus of claim 13 further comprising a controller configured and arranged for generating control signals that activate the pump to generate a positive pressure in the chamber and a pressure sensor fluidically connected to the chamber and having an electrical output connected to an input of the controller, the pressure sensor providing an electrical signal to the controller indicative of a sensed pressure in the chamber, wherein the controller transmits control signals to the pump based on the sensed pressure.

15. The apparatus of claim 12, wherein the pressure generating device is configured and arranged for generating a positive pressure within the chamber that is at or below a predetermined threshold of about 6 atm, the positive pressure being sufficient to cause the biological material, if present in the chamber, to discharge through the outlet, wherein the predetermined threshold of about 6 atm is a pressure above which the biological material has relatively low viability as a tissue graft following discharge from the outlet into a graft site in a subject.

16. The apparatus of claim 15, wherein the positive pressure is maintained such that the velocity of the biological material discharging from the outlet is up to about 265 cm/sec.

17. The apparatus of claim 15, wherein the positive pressure is maintained such that the flow rate of the biological material being discharged from the outlet is below 3 ml/sec.

18. The apparatus of claim 15, wherein the positive pressure is about 4 atm.

19. The apparatus of claim 1, wherein the retention matrix includes both the hydrophilic matrix and the lipophilic matrix.

20. The apparatus of claim 19, wherein the hydrophilic matrix is positioned downstream from the lipophilic matrix within the chamber.

21. The apparatus of claim 1, wherein the first outlet of the chamber is configured and arranged to permit discharge from the chamber of a portion of the biological material that does not pass through the filter.

22. The apparatus of claim 1, wherein the chamber has a second waste outlet, wherein the inlet is fluidly connected to the second waste outlet along a second flow path through both the filter and the retention matrix.

23. The apparatus of claim 22, wherein the filter is disposed between the second waste outlet and the retention matrix.

24. The apparatus of claim 22, wherein the retention matrix and the filter are configured and arranged such that the waste fraction of the biological material flows through both the filter and the retention matrix to the second waste outlet.

25. A method comprising:

obtaining the apparatus of claim 12;

loading biological material into the chamber of the apparatus; and causing the pressure generating device to generate a positive pressure within the chamber that is at or below a predetermined threshold of about 6 atm to cause the biological material to discharge through the outlet.

26. The method of claim 25, wherein the biological material comprises adipose tissue and the method further comprises positioning the outlet such that the biological material discharges into a graft site of a subject.

27. The method of claim 26, wherein the biological material is obtained from the subject.

28. The method of claim 27, wherein the biological material is obtained by extraction of adipose tissue from the abdomen, thigh, flank region, or gluteal region of the subject or by extraction of lipoaspirate comprising such adipose tissue of the subject.

29. The method of claim 26, wherein the biological material is obtained from the subject and processed prior to loading into the chamber to at least partially remove oil, blood, tumescent fluid, stromal cells, extracellular material or cell debris from the biological material.

30. An apparatus comprising:

a chamber having at least one outlet positioned at a distal end of the chamber and an opening at a proximal end of the chamber;

a retention matrix within the chamber configured and arranged for contacting a biological material, when present in the chamber, such that a fraction of the biological material is retained in the retention matrix;

a filter within the chamber that is configured and arranged for contacting the biological material, when present in the chamber, such that a waste fraction of the biological material passes through the filter; and a plunger that passes through the opening and is movably disposed within the chamber; wherein the plunger controls a pressure within the chamber.

31. The apparatus of claim 30, wherein displacement of the plunger within the chamber toward the distal end generates a positive pressure in the chamber.

32. The apparatus of claim 31, wherein the plunger comprises a force-limiting clutch configured and arranged to limit, to a predetermined threshold, a maximum pressure developed in the chamber by depressing a rod of the plunger toward the distal end of the chamber, wherein the force-limiting clutch has a frictional interface mechanically coupling the rod to a piston.

33. The apparatus of claim 31, further comprising a plunger displacement device configured and arranged for displacing the plunger toward the distal end of the chamber at a rate that results in the positive pressure in the chamber being at or below a predetermined threshold while discharging the biological material from the outlet.

34. The apparatus of claim 33 further comprising a controller configured and arranged for generating control signals that activate the plunger displacement device to displace the plunger toward the distal end of the chamber, and a pressure sensor fluidically connected to the chamber and having an electrical output connected to an input of the controller, the pressure sensor providing an electrical signal to the controller indicative of a sensed pressure in the chamber, wherein the controller transmits control signals to the plunger displacement device based on the sensed pressure.

35. The apparatus of claim 30, further comprising a membrane stabilization agent (MSA) in the chamber.

36. The apparatus of claim 30, wherein the retention matrix comprises at least one selected from the group of a lipophilic matrix that retains lipids from the biological material and a hydrophilic matrix that retains water from the biological material.

37. The apparatus of claim 36, wherein the retention matrix includes both a lipophilic matrix and a hydrophilic matrix.

38. The apparatus of claim 37, wherein the hydrophilic matrix is positioned downstream from the lipophilic matrix within the chamber.

39. The apparatus of claim 30, wherein the retention matrix comprises a hydrogel.

40. An apparatus comprising
a chamber having an inlet and a first outlet;
a retention matrix within the chamber configured and arranged for contacting a biological material, when present in the chamber, such that a fraction of the biological material is retained in the retention matrix, wherein the retention matrix comprises a hydrogel, and
a filter within the chamber that is configured and arranged for contacting the biological material, when present in the chamber, such that a waste fraction of the biological material passes through the filter, wherein the inlet is fluidly connected to the first outlet along a first flow path that does not pass through the filter.

* * * * *